(12) United States Patent
Rangaramanujam et al.

(10) Patent No.: US 10,463,609 B2
(45) Date of Patent: *Nov. 5, 2019

(54) DENDRIMERS FOR SUSTAINED RELEASE OF COMPOUNDS

(75) Inventors: Kannan Rangaramanujam, Novi, MI (US); Raymond Iezzi, Troy, MI (US); Bharath Rajaguru, Detroit, MI (US); Sujatha Kannan, Novi, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 1110 days.

This patent is subject to a terminal disclaimer.

(21) Appl. No.: 12/681,516

(22) PCT Filed: Oct. 6, 2008

(86) PCT No.: PCT/US2008/078988
§ 371 (c)(1),
(2), (4) Date: Apr. 2, 2010

(87) PCT Pub. No.: WO2009/046446
PCT Pub. Date: Apr. 9, 2009

(65) Prior Publication Data
US 2011/0034422 A1     Feb. 10, 2011

Related U.S. Application Data

(60) Provisional application No. 61/135,809, filed on Jul. 23, 2008, provisional application No. 60/997,987, filed on Oct. 5, 2007.

(51) Int. Cl.
*A61K 9/00* (2006.01)
*A61K 31/7088* (2006.01)
(Continued)

(52) U.S. Cl.
CPC .......... *A61K 9/0048* (2013.01); *A61K 9/0051* (2013.01); *A61K 9/1647* (2013.01);
(Continued)

(58) Field of Classification Search
CPC ........ A61K 47/48253; A61K 47/48207; A61K 9/0048; A61K 31/7088; A61K 47/6935;
(Continued)

(56) References Cited

U.S. PATENT DOCUMENTS

| 4,507,466 A | 3/1985 | Tomalia et al. |
| 4,558,120 A | 12/1985 | Tomalia et al. |

(Continued)

FOREIGN PATENT DOCUMENTS

| WO | 2003080121 | 10/2003 |
| WO | 2004106411 | 12/2004 |

(Continued)

OTHER PUBLICATIONS

Choi et al., International Journal of Pharmaceutics, 320: 171-178 (2006).*

(Continued)

*Primary Examiner* — Trevor Love
(74) *Attorney, Agent, or Firm* — Pabst Patent Group LLP

(57) ABSTRACT

Dendrimer-based compositions and methods are provided, that are useful for administering pharmaceutical compositions to target cells and tissues for treatment of ocular diseases including macular degeneration, diabetic retinopathy, and retinitis pigmentosa.

7 Claims, 12 Drawing Sheets

(51) Int. Cl.
| | | |
|---|---|---|
| A61K 47/69 | (2017.01) | |
| A61K 47/59 | (2017.01) | |
| A61K 31/65 | (2006.01) | |
| A61K 31/58 | (2006.01) | |
| A61K 9/50 | (2006.01) | |
| C08L 101/00 | (2006.01) | |
| C08L 79/02 | (2006.01) | |
| C08G 83/00 | (2006.01) | |
| C08G 73/02 | (2006.01) | |
| A61K 9/51 | (2006.01) | |
| A61L 9/16 | (2006.01) | |
| B82Y 5/00 | (2011.01) | |
| A61K 9/16 | (2006.01) | |

(52) U.S. Cl.
CPC .......... *A61K 9/5031* (2013.01); *A61K 9/5153* (2013.01); *A61K 31/58* (2013.01); *A61K 31/65* (2013.01); *A61K 31/7088* (2013.01); *A61K 47/595* (2017.08); *A61K 47/6935* (2017.08); *C08G 73/028* (2013.01); *C08G 83/003* (2013.01); *C08L 79/02* (2013.01); *C08L 101/005* (2013.01); *B82Y 5/00* (2013.01)

(58) Field of Classification Search
CPC ...... A61K 47/595; A61K 31/65; A61K 31/58; A61K 9/5031; A61K 9/5153; A61K 9/1647; A61K 9/0051; C08L 101/005; C08L 78/02; B82Y 5/00; C08G 83/003; C08G 73/028
See application file for complete search history.

(56) References Cited

U.S. PATENT DOCUMENTS

| | | | |
|---|---|---|---|
| 4,568,737 | A | 2/1986 | Tomalia et al. |
| 4,587,329 | A | 5/1986 | Tomalia et al. |
| 5,714,166 | A | 2/1998 | Tomalia et al. |
| 6,160,084 | A | 12/2000 | Langer |
| 6,726,918 | B1* | 4/2004 | Wong ............... A61K 9/0051 424/400 |
| 2002/0068795 | A1 | 6/2002 | Won et al. |
| 2003/0180250 | A1* | 9/2003 | Chauhan et al. ......... 424/78.05 |
| 2004/0151754 | A1* | 8/2004 | Ashton ..................... 424/427 |
| 2007/0020224 | A1 | 1/2007 | Vetter |
| 2007/0088014 | A1 | 4/2007 | Edelman et al. |
| 2007/0280902 | A1* | 12/2007 | Rabinovich-Guilatt ............ A61K 9/0014 424/85.1 |

FOREIGN PATENT DOCUMENTS

| | | |
|---|---|---|
| WO | 2006033766 | 3/2006 |
| WO | WO2007089607 | 8/2007 |

OTHER PUBLICATIONS

MedlinePlus, accessed at http://www.nlm.nih.gov/medlineplus/ency/article/003040.htm Jan. 23, 2013.*
Eye Disorders: Merck Manual Home Edition, Merck Sharp & Dohme Corp., 2010-2011 (9 pages), accessed at http://www.merckmanuals.com/home/eye_disorders.html Jan. 23, 2013.*
Singh Chauhan et al., Journal of Drug Targeting, 12: 575-583 (2004).*
Khandare et al., Bioconjugate Chemistry, 16: 330-337 (2005).*
Dutta et al., Journal of Drug Targeting, 15: 89-98 (Jan. 2007).*
Rajaguru et al., American Institute of Chemical Engineers 2006 Annual Meeting, Session #477d—(22b) Nov. 2006.*
Iezzi et al., Biomaterials, 33: 979-988 (2012).*
Buddi et al., Retinal Physician (2004), accessed online at http://www.retinalphysician.com/articleviewer.aspx?articleID=100022,May 6, 2015.*
Thomas et al., Journal of Medicinal Chemistry, 48: 3729-3735 (2005).*
Hollis et al. (Journal of Drug Targeting, 15: 83-88 (2007).*
Kukowska-Latallo et al. (PNAS, 93: 4897-4902 (1996).*
Dennig et al., Review in Molecular biotechnology, 90: 339-347 (2002).*
Kansara et al., Drug Delivery Research Advances, Mashkevih, Ed. Nova Science Publishers, Inc. (2007) pp. 4-6.*
Trehin et al., Neoplasia, 8: 302-311 (Year: 2006).*
Klajnert et al, Interactions between PAMAM dendrimers and bovine serum albumin, 2003, Biochimica et Biophysica Acta 1648, 115-126. (Year: 2003).*
Chang et al., "Effects of Glucocorticoids on Fas Gene Expression in Bovine Blood Neutrophils," *J. Endocrinol.* 183:569-83, 2004.
Chang et al., "Inhibition of Microglial Nitric Oxide Production by Hydrocortisone and Glucocorticoid Precursors," *Neurochem Res.* 25(7):903-8, 2000.
Chang et al., "Minocycline Partially Inhibits Caspase-3 Activation and Photoreceptor Degeneration After Photic Injury," *Ophthalmic Res.* 37:202-13, 2005.
Cox, "Glucocorticoid Treatment Inhibits Apoptosis in Human Neutrophils. Separation of Survival and Activation Outcomes," *J. Immunol.* 154:4719-25, 1995.
De Kozak et al., "Tumor Necrosis Factor and Nitric Oxide Production by Resident Retinal Glial Cells From Rats Presenting Hereditary Retinal Degeneration," *Ocul. Immunol. Inflamm.* 5(2):85-94, 1997.
Dierks et al., "Electroretinographic Effects of an Intravitreal Injection of Triamcinolone in Rabbit Retina," *Arch. Ophthalmol.* 123(11):1563-69, 2005.
Dinkel et al., "Novel Glucocorticoid Effects on Acute Inflammation in the CNS," *J. Neurochem.* 84(4):705-16, 2003.
Drew et al., "Inhibition of Microglial Cell Activation by Cortisol," *Brain Res. Bull.* 52(5):391-6, 2000.
Dykens et al., "Photoreceptor Preservation in the S334ter Model of Retinitis Pigmentosa by a Novel Estradiol Analog," *Biochem. Pharmacol.* 68(10):1971-84, 2004.
Eversole et al., "Protective Effect of the 21-Aminosteroid Lipid Peroxidation Inhibitor Tirilazad Mesylate (U74006F) on Hepatic Endothelium in Experimental Hemorrhagic Shock," *Circ. Shock* 40(2):125-31, 1993.
Gal et al., "Mutations in MERTK, the Human Orthologue of the RCS Rat Retinal Dystrophy Gene, Cause Retinitis Pigmentosa," *Nat. Genet.* 26(3):270-1, 2000.
Glezer et al., "Glucocorticoids: Protectors of the Brain During Innate Immune Responses," *Neuroscientist* 10(6):538-52, 2004.
Gonzalez et al., "Glucocorticoids Antagonize AP-1 by Inhibiting the Activation/Phosphorylation of JNK Without Affecting Its Subcellular Distribution," *J. Cell Biol.* 150(5):1199-208, 2000.
Green and Kroemer, "The Pathophysiology of Mitochondrial Cell Death," *Science* 305(5684):626-9, 2004.
Gupta et al., "Activated Microglia in Human Retinitis Pigmentosa, Late-Onset Retinal Degeneration, and Age-Related Macular Degeneration," *Exp. Eye Res.* 76(4):463-71, 2003.
Hall et al., "The Phagocytosis of Rod Outer Segments Is Inhibited by Drugs Linked to Cyclic Adenosine Monophosphate Production," *Invet. Ophthamol. & Vis. Sci.* 34(8):2392-240, 1993.
Horwitz et al., "Efficacy of Lipid Soluble, Membrane-Protective Agents Against Hydrogen Peroxide Cytotoxicity in Cardiac Myocytes," *Free Radic. Biol. Med.* 21(6):743-53, 1996.
Hughes et al., "Minocycline Delays Photoreceptor Death in the RDS Mouse Through a Microglia-Independent Mechanism," *Exp. Eye Res.* 78(6):1077-84, 2004.
Ignarro, "Lysosome Membrane Stabilization in Vivo: Effects of Steroidal and Nonsteroidal Anti-Inflammatory Drugs on the Integrity of Rat Liver Lysosomes," *J. Pharmacol Exp. Ther.* 182(1):179-88, 1972.
Islam et al., "HPLC Separation of Different Generations of Poly(Amidoamine) Dendrimers Modified With Various Terminal Groups," *Anal. Chem.* 77:2063-2070, 2005.

(56) References Cited

OTHER PUBLICATIONS

Jaffe et al., "Fluocinolone Acetonide Implant (Retisert) for Noninfectious Posterior Uveitis: Thirty-Four-Week Results of a Multicenter Randomized Clinical Study," Ophthalmol. 113:1020-1027, 2006.
Jaffe et al., "Fluocinolone Acetonide Sustained Drug Delivery Device to Treat Severe Uveitis," Ophthalmol. 107:2024-2033, 2000.
Jaffe et al., "Safety and Pharmacokinetics of an Intraocular Fluocinolone Acetonide Sustained Delivery Device," Invest. Ophthalmol. & Vis. Sci. 41:3569-3575, 2000.
Jou et al., "Gangliosides Trigger Inflammatory Responses via TLR4 in Brain Glia," Am. J. Pathol. 168:1619-1630, 2006.
Kannan et al., "Dynamics of Cellular Entry and Drug Delivery by Dendritic Polymers Into Human Lung Epithelial Carcinoma Cells," J. Biomaterial Science: Polymer Ed. 15:311-330, 2004.
Katai et al., "Caspaselike Proteases Activated in Apoptotic Photoreceptors of Royal College of Surgeons Rats," Invest. Ophthalmol. Vis. Sci. 40:1802-7, 1999.
Khandare, J. et al., "Synthesis, Cellular Transport, and Activity of Polyamidoamine Dendrimer-Methylprednisolone Conjugates," Bioconjugate Chem. 16:330-337, 2005.
Kiefer et al., "Effects of Dexamethasone on Microglial Activation in Vivo: Selective Downregulation of Major Histocompatibility Complex Class II Expression in Regenerating Facial Nucleus," J. Neuroimmunol. 34(2):99-108, 1991.
Kolhe et al., "Preparation, Cellular Transport, and Activity of Polyamidoamine-Based Dendritic Nanodevices With a High Drug Payload," Biomaterials 27:660-669, 2006.
Lehmann et al. "Inhibition of Tumor Necrosis Factor-Alpha Release in Rat Experimental Endotoxemia by Treatment With the 21-Aminosteroid U-74389G," Crit. Care Med. 27(6):1164-7, 1999.
Lettéron et al., "Glucocorticoids Inhibit Mitochondrial Matrix Acyl-CoA Dehydrogenases and Fatty Acid—Oxidation," Am. J. Physiol. 272: G1141-1150, 1997.
Liang et al., "Long-Term Protection of Retinal Structure but not Function Using RAAV.CNTF in Animal Models of Retinitis Pigmentosa," Mol. Ther. 4(5):461-72, 2001.
Lieb et al., "Inhibition of LPS-Induced iNOS and NO Synthesis in Primary Rat Microglial Cells," Neurochem. Int. 42(2):131-7, 2003.
Marano et al., "Dendrimer Delivery of an Anti-VEGF Oligonucleotide Into the Eye: A Long-Term Study into Inhibition of Laser-Induced CNV, Distribution, Uptake and Toxicity," Nature Gene Therapy 12:1544-1550, 2005.
Marchetti et al., "Mitochondrial Permeability Transition Is a Central Coordinating Event of Apoptosis," J. Exp. Med. 184(3):1155-60, 1996.
Min et al., "Gangliosides Activate Microglia via Protein Kinase C and NADPH Oxidase," Glia 48:197-206, 2004.
Panyam et al., "Fluorescence and Electron Microscopy Probes for Cellular and Tissue Uptake of Poly(D,L-Lactide-Co-Glycolide) Nanoparticles," Int. J. Pharm. 262:1-11, 2003.
Panyam et al., "Polymer Degradation and in Vitro Release of a Model Protein From Poly(D,L-Lactide-Co-Glycolide) Nano- and Microparticles," J. Control. Release 92:173-187, 2003.
Perumal et al., "The Effect of Surface Functionality on Cellular Trafficking of Dendrimers," Biomaterials 29:3469-3476, 2008.
Pyo et al., "Gangliosides Activate Cultured Rat Brain Microglia," J. Biol. Chem. 274:34584-34589, 1999.
Sahoo et al., "Residual Polyvinyl Alcohol Associated With Poly (D,L-Lactide-Co-Glycolide) Nanoparticles Affects Their Physical Properties and Cellular Uptake," J. Control. Release 82:105-114, 2002.
Sakurai et al., "Effect of Particle Size of Polymeric Nanospheres on Intravitreal Kinetics," Ophthalmic Res. 33:31-36, 2001.
Sanvicens et al., "Oxidative Stress-Induced Apoptosis in Retinal Photoreceptor Cells Is Mediated by Calpains and Caspases and Blocked by the Oxygen Radical Scavenger CR-6," J. Biol. Chem. 279(38):39268-78, 2004.
Shimazawa et al., "Neuroprotective Effects of Minocycline Against in Vitro and in Vivo Retinal Ganglion Cell Damage," Brain Res. 1053:185-94, 2005.
Sieving et al., "Ciliary Neurotrophic Factor (CNTF) for Human Retinal Degeneration: Phase I Trial of CNTF Delivered by Encapsulated Cell Intraocular Implants," Proc. Natl. Acad. Sci. USA 103(10):3896-901, 2006.
Spierings et al. "Connected to Death: The (Unexpurgated) Mitochondrial Pathway of Apoptosis," Science 310(5745):66-7, 2005.
Tanito et al. "Cytoprotective Effects of Geranylgeranylacetone Against Retinal Photooxidative Damage," J. Neurosci. 25(9):2396-404, 2005.
Tao, "Application of Encapsulated Cell Technology for Retinal Degenerative Diseases," Expert Opin. Biol. Ther. 6(7):717-26, 2006.
Tao et al., "Encapsulated Cell-Based Delivery of CNTF Reduces Photoreceptor Degeneration in Animal Models of Retinitis Pigmentosa," Invest. Ophthalmol. Vis. Sci. 43(10):3292-8, 2002.
Thanos, "Sick Photoreceptors Attract Activated Microglia from the Ganglion Cell Layer: A Model to Study the Inflammatory Cascades in Rats With Inherited Retinal Dystrophy," Brain Res. 588(1):21-8, 1992.
Thanos et al., "The Migratory Potential of Vitally Labelled Microglial Cells Within the Retina of Rats With Hereditary Photoreceptor Dystrophy," Int. J. Dev. Neurosci. 11(5):671-80, 1993.
Tomalia et al., "Starburst Dendrimers: Molecular-Level Control of Size, Shape, Surface Chemistry, Topology, and Flexibility From Atoms to Macroscopic Matter," Agnew. Chem. Int. Ed. Engl. 29:138-175, 1990.
Tso et al., "Apoptosis Leads to Photoreceptor Degeneration in Inherited Retinal Dystrophy of RCS Rats," Invest. Ophthalmol. Vis. Sci. 35(6):2693-9, 1994.
Wang et al., "The 21-Aminosteroid Tirilazad Mesylate Protects Against Liver Injury via Membrane Stabilization not Inhibition of Lipid Peroxidation," J. Pharm. Exp. Ther. 277(2):714-20, 1996.
Wenzel et al. "Prevention of Photoreceptor Apoptosis by Activation of the Glucocorticoid Receptor," Invest. Ophthalmol. Vis. Sci. 42(7):1653-9, 2001.
Yang et al., "Dendrimers for Pharmaceutical and Biomedical Applications," J. Biomater. Sci. Polymer Ed. 17:3-19, 2006.
Yang et al., "Fas and Activation-Induced Fas Ligand Mediate Apoptosis of T Cell Hybridomas: Inhibition of Fas Ligand Expression by Retinoic Acid and Glucocorticoids," J. Exp. Med. 181:1673-82, 1995.
Yin et al., "Architectural Copolymers: Rod-Shaped, Cylindrical Dendrimers," J. Am. Chem. Soc. 120:2678, 1998.
Zeiss et al., "CNTF Induces Dose-Dependent Alterations in Retinal Morphology in Normal and Rcd-1 Canine Retina," Exp. Eye Res. 82(3):395-404, 2006.
Zeng,. et al., "Identification of Sequential Events and Factors Associated With Microglial Activation, Migration, and Cytotoxicity in Retinal Degeneration in rd Mice," Invest. Ophthalmol. Vis. Sci. 46(8):2992-9, 2005.
Zhang et al., "Neuroprotection of Photoreceptors by Minocycline in Light-Induced Retinal Degeneration," Invest. Ophthalmol. Vis. Sci. 45:2753-9, 2004.
Chen, et al.,"Interaction of Dendrimers (Artificial Proteins) with Biological Hydroxyapatite Crystals", J. Dent. Res., vol. 82, No. 6, 2003, pp. 443-448.
Duncan and Izzo,"Dendrimer Biocompatibility and Toxicity", Adv. Drug Del. Reviews, vol. 57, 2005, pp. 2215-2237.
Esfand, et al.,"Poly(amidoamine) (PAMAM) Dendrimers: From Biomimicry to Drug Delivery and Biomedical Applications", DDT, vol. 6, No. 8, 2001, pp. 427-436.
Gurdag, et al.,"Activity of Dendrimer-Methotrexate Conjugates on Methotrexate-Sensitive and -Resistant Cell Lines", Bioconjugate Chem., vol. 17, 2006, pp. 275-283.
Jiang, et al.,"Tumor Imaging by Means of Proteolytic Activation of Cell-Penetrating Peptides", PNAS, vol. 101, No. 51, 2004, pp. 17867-17872.
Kobayashi, et al.,"3D-Micro-MR Angiography of Mice Using Macromolecular MR Contrast Agents With Polyamidoamine Dendrimer

(56) References Cited

OTHER PUBLICATIONS

Core With Reference to Their Pharmacokinetic Properties", Magnetic Resonance in Medicine, vol. 45, 2001, pp. 454-460.
Kobayashi, et al.,"Comparison of the Macromolecular MR Contrast Agents with Ethylenediamine-Core Versus Ammonia-Core Generation-6 Polyamidoamine Dendrimer", Bioconjugate Chem., vol. 12, 2001, pp. 100-107.
Kukowska-Latallo, et al., "Nanoparticle Targeting of Anticancer Drug Improves Therapeutic Response in Animal Model of Human Epithelial Cancer", Cancer Research, vol. 65, No. 12, 2005, pp. 5317-5324.
Landers, et al.,"Prevention of Influenza Pneumonitis by Sialic Acid-Conjugated Dendritic Polymers", J. of Infectious Diseases, vol. 186, 2002, pp. 1222-1230.
Liang, et al., "PAMAM Dendrimers and Branched Polythyleneglycol (nanoparticles) Prodrugs of (-)-[beta]-D-(2R, 4R)Dioxolane-Thymine (DOT) and Their Anti-HIV Activity", Antiviral Chemistry and Chemotherapy 2006 GB, vol. 17, No. 6, 2006, pp. 321-329.
Office Action dated May 25, 2015 in Indian Application No. 1247/KOLNP/2010.
Office Action dated Jun. 3, 2013 in Japanese Application No. 2010-528216.
Office Action dated Aug. 6, 2014 in Canadian Application No. 2,701,291.
Pikkemaat, et al.,"Dendritic PARACEST Contrast Agents for Magnetic Resonance Imaging", Contrast Media Mol. Imaging, vol. 2, 2007, pp. 229-239.
Sato, et al.,"Pharmacokinetics and Enhancement Patterns of Macromolecular MR Contrast Agents With Various Sizes of Polyamidoamine Dendrimer Cores", Magnetic Resonance in Medicine, vol. 46, 2001, pp. 1169-1173.
Sato, et al.,"Tumor Targeting and Imaging of Intraperitoneal Tumors by Use of Antisense Oligo-DNA Complexed with Dendrimers and/or Avidin in Mice1", Clinical Cancer Research, vol. 7, 2001, pp. 3606-3612.
Search Report and Written Opinion dated Apr. 15, 2009 in International Application No. PCT/US2008/078988.
Search Report dated Jul. 29, 2014 in European Application No. 08835693.6.
Tomalia, et al., "Dendrimers as Multi-Purpose Nanodevices for Oncology Drug Delivery and Diagnostic Imaging", Biochemical Society Transactions, vol. 35, No. 1, 2007, pp. 61-67.
Vincent, et al.,"Efficacy of Dendrimer-Mediated Angiostatin and Timp-2 Gene Delivery on Inhibition of Tumor Growth and Angiogenesis: In Vitro and In Vivo Studies", Int. J. Cancer, vol. 105, 2003, pp. 419-429.
Xiangyang, et al., "Dendrimer-Entrapped Gold Nanoparticles as a Platform for Cancer-Cell Targeting and Imaging", Small, vol. 3, No. 7, Jul. 2, 2007, pp. 1245-1252.
Zhang, et al., "Conjugation of Polyamidoamine Dendrimers on Biodegradable Mircoparticles for Nonviral Gene Delivery", Bioconjugate Chemistry, vol. 18, No. 6, 2007, pp. 2068-2076.
Office Action dated Feb. 1, 2016 for European Application No. 08835693.6.

Hall, et al., ",Antioxidant effects in brain and spinal cord injury", J Neurotrauma, 9(Supp 1):165-72 (1992) Abstract Only.
Inapagolla, et al,, "In vivo efficacy of dendrimer-methylprednisolone conjugate formulation for the treatment of lung inflammation", Intl J Pharma., 399:140-7 (2010).
Wells, et al., "Neuroprotection by minocycline facilitates significant recovery from spinal cord injury in mice", Brain, 126:1628-37 (2003).
Alghadyan, et al., "Diabetic retinopathy—An update", Saudi J Ophthalmology, 25:99-111 (2011).
Chauhan, et al., "Solubility enhancement of indomethacin with poly(amidoamine) dendrimers and targeting to inflammatory regions of arthritic rats", J Drug Targeting, 12(9-10):575-83 (2004).
Dai et al., "Intrinsic targeting of inflammatory cells in the brain by polyamidoamine dendrimers upon subarachnoid administration," Nanomedicine, 5:1317-1329 (2010).
Dani, et al., "Prophylactic ibuprofen for the prevention of intraventricular hemorrhage among preterm infants: A multicenter, randomized study", Pediatrics, 115(6):1-6 (2005).
Gomez et al., "NMR characterization of fourth-generation PAMAM dendrimers in the presence and absence of palladium dendrimer-encapsulated nanoparticles," JACS, 131:341-350 (2008).
Lambat et al., "An investigation into the neuroprotective properties of ibuprofen," Metabolic Brain Disease, 15:249-256 (2000).
Laube, et al., "Deployment of antioxidant cox-2inhibitors as radioprotective agents for radiation therapy-a hypothesis-driven", Antioxidants, 5:14:doi:10.3390antiox502014 (2016).
Shaaya et al., "Anhydride prodrugs for nonsteroidal anti-inflammatory drugs," Pharmaceutical Research, 20:205-211 (2003).
Shi et al., "Dendrimer-entrapped gold nanoparticles as a platform for cancer-cell targeting and imaging", Small, 3:1245-1252 (2007).
Wilkinson, et al., "Ibuprofen attenuates oxidative damage through nox2 inhibition in Alzheimer's disease", Neurobiology Aging, 33:197e21-197 (2012).
Yates, "Corticosteroids in head injury: It's time for a large simple randomized trial", BMJ, 321:121-9 (2000).
Akaishi et al., "Quantitative Analysis of Major Histocompatibility Complex Class II-Positive Cells in Posterior Segment of Royal College of Surgeons Rat Eyes," *Jpn. J. Ophthalmology* 42:357-62, 1998.
Augustin et al., "Effects of Allopurinol and Steroids on Inflammation and Oxidative Tissue Damage in Experimental Lens Induced Uveitis: A Biochemical and Morphological Study," *Br. J. Ophthalmol.* 80(5):451-7, 1996.
Behl et al., "Neuroprotection Against Oxidative Stress by Estrogens: Structure-Activity Relationship," *Mol. Pharmacol.* 51(4):535-41, 1997.
Bell et al., "Effects of Intrauterine Inflammation on Developing Rat Brain," *J. Neurosci. Res.* 70:570-579, 2002.
Berson et al., "Vitamin A Supplementation for Retinitis Pigmentosa," *Arch. Ophthalmol.* 111(11):1456-59, 1993.
Bourges et al., "Ocular Drug Delivery Targeting the Retina and Retinal Pigment Epithelium Using Polylactide Nanoparticles," *Invest. Opthalmol. & Vis. Sci.* 44:3562-3569, 2003.
Carmody et al., "Reactive Oxygen Species as Mediators of Photoreceptor Apoptosis in Vitro," *Exp. Cell Res.* 248(2):520-30, 1999.

\* cited by examiner

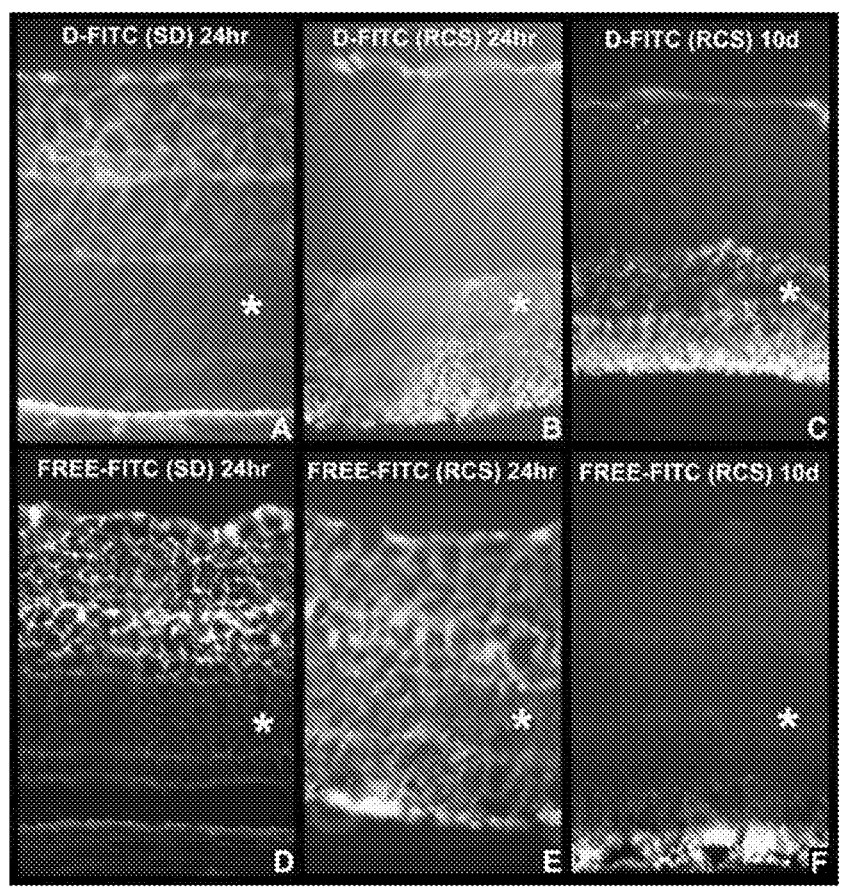

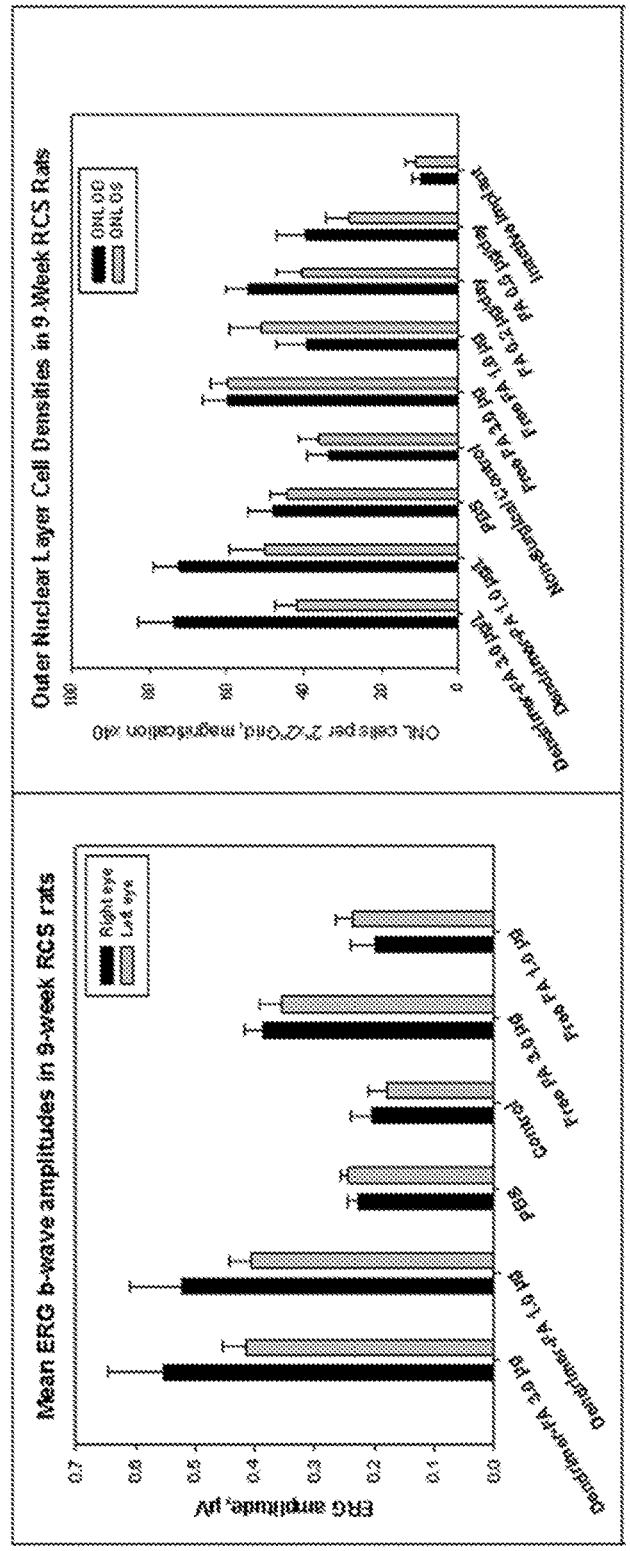

FIG. 7
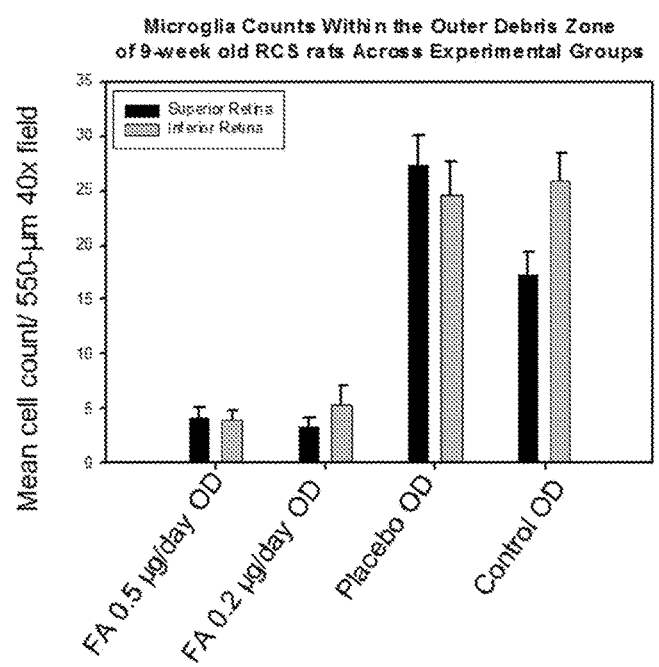
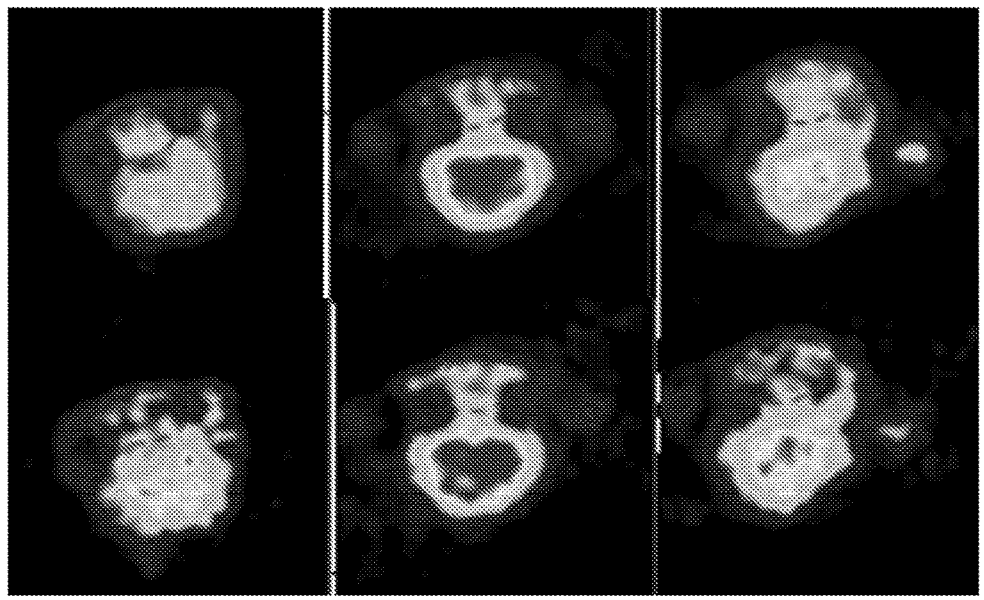
FIG. 8A  FIG. 8B  FIG. 8C
FIG. 8D  FIG. 8E  FIG. 8F

FIG. 11A    FIG. 11B
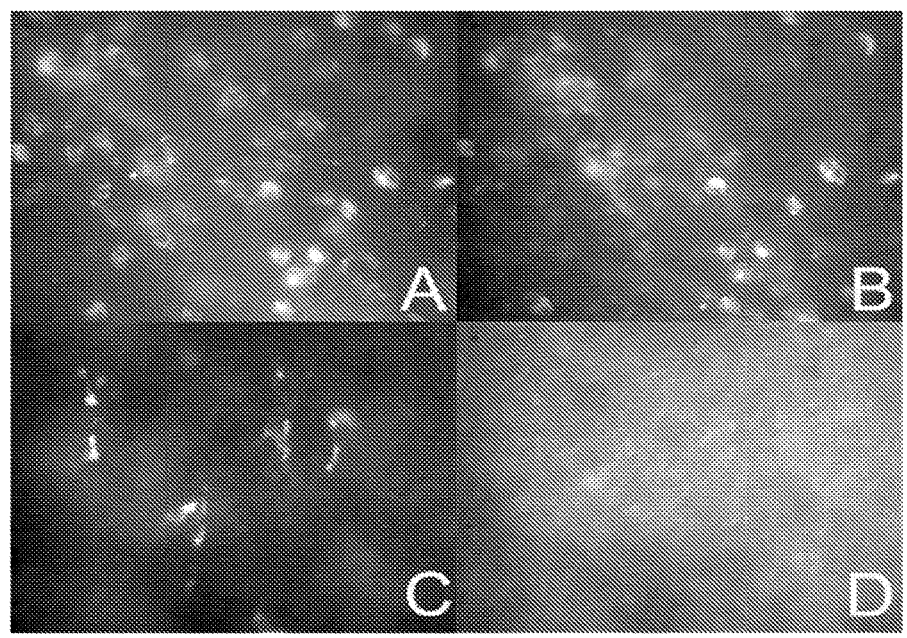
FIG. 11C    FIG. 11D
FIG. 12A    FIG. 12B
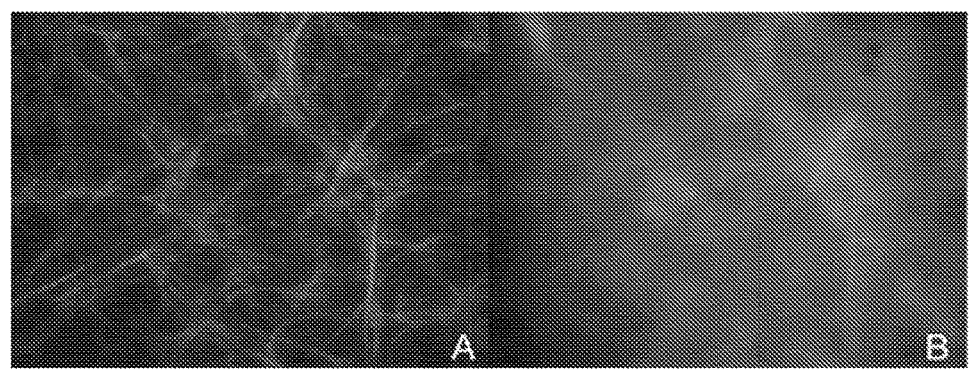

FIG. 13A    FIG. 13B
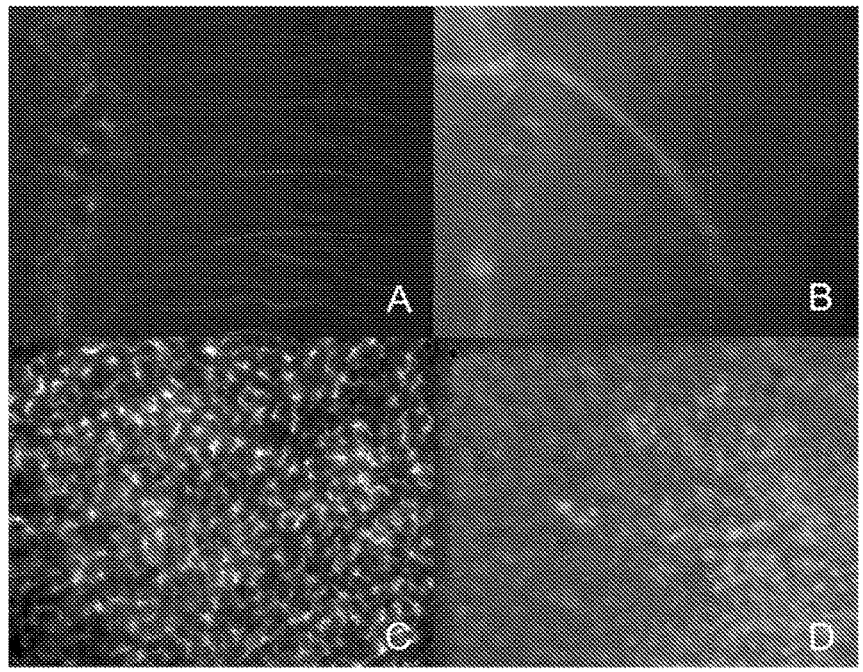
FIG. 13C    FIG. 13D
FIG. 14
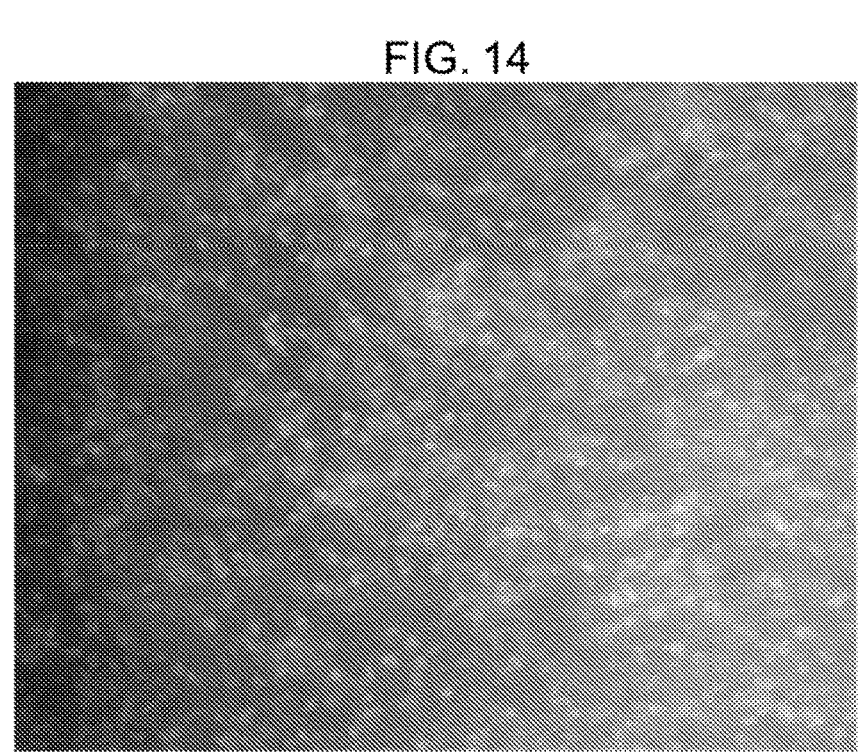

FIG. 15A
FIG. 15B
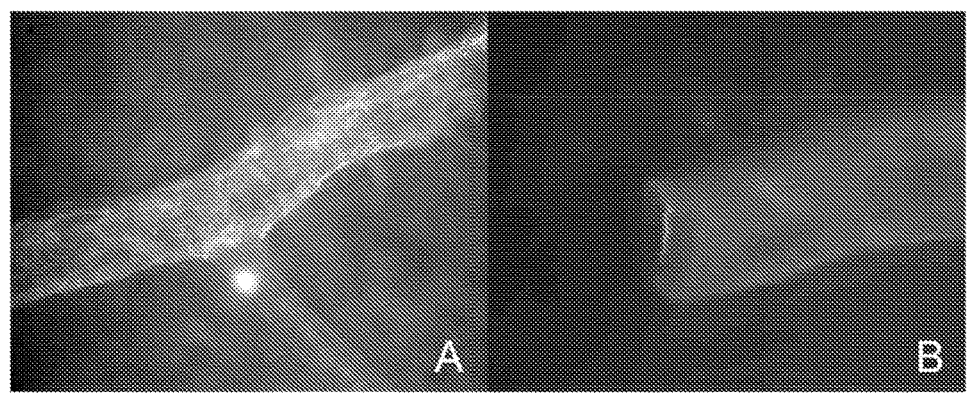
FIG. 16A
FIG. 16B
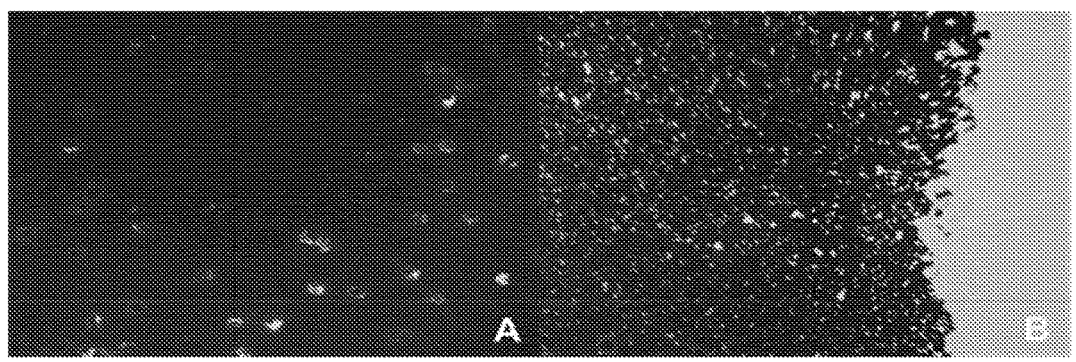

DENDRIMERS FOR SUSTAINED RELEASE OF COMPOUNDS

CROSS REFERENCE TO RELATED APPLICATIONS

This application is a national phase of PCT/US2008/078988, filed on Oct. 6, 2008, which claims the benefit of U.S. provisional patent application number 61/135, 809, filed Jul. 23, 2008, and U.S. provisional patent application number 60/997,987, filed Oct. 5, 2007, the entire disclosures of which are incorporated herein by reference.

STATEMENT REGARDING FEDERALLY SPONSORED RESEARCH OR DEVELOPMENT

This invention was made with government support under 1067323 awarded by the National Science Foundation. The government has certain rights in the invention.

FIELD OF THE INVENTION

The present invention relates to dendrimer-based compositions and methods useful for administering pharmaceutical compositions to target cells and tissues for suppressing neuroinflammation in disease states, including macular degeneration.

BACKGROUND

A common pathway in many human disease states is microglia-mediated inflammation. Microglia are tissue-resident macrophages found in the retina and the central nervous system. Microglial cells constitute about ten to twenty percent of the cells in the adult brain. Under normal conditions, these cells are constitutively suppressed by endogenous cortisol. The cells become activated in the form of phagocytes and cytotoxic cells in the presence of a variety of stimuli. These stimuli include trauma, infection, inflammation, ischemia, lipopolysaccharides, reactive oxygen species, and damaged cell membranes. Once microglia are activated, they can migrate and recruit other microglia to the original site of damage. Malfunctioning cells can be killed by the release of tumor necrosis factor alpha (TNF-α), reactive oxygen species (ROS), and proteases. The resulting cell debris is phagocytized by the microglia cells.

Secondary cell damage occurs in a process referred to as bystander lysis: nearby healthy cells are destroyed in the toxic extracellular milieu created by the activated microglia. This amplifies the cell damage beyond the cells affected by the underlying pathologic event, and turns the remedy—the activated microglial cells—into a pathologic system in its own right.

The cascading pattern of primary pathology, response by microglial cells, and subsequent secondary pathology has been observed in a broad range of human diseases, including diseases of the eye. An essential element of sight is a functioning retina. The retina can be likened to the "film" of the eye. It converts light rays into electrical signals and sends them to the brain through the optic nerve. The sides of the retina are responsible for peripheral vision. The center area, called the macula, is used for fine central vision and color vision. The retina is where many problems leading to vision loss occur. Three of the leading causes of blindness due to retina damage associated with neuroinflammation are retinitis pigmentosa, macular degeneration and diabetic retinopathy, the leading cause of blindness in African Americans is glaucoma a degenerative process of the optic nerve and retina that involves neuroinflammation and microglial cell activation within the optic nerve that connects the retina to the brain. Other important retinal diseases that are associated with neuroinflammation include uveitis, auto-immune photoreceptor degenerations and infection.

From a clinical perspective, retinitis pigmentosa, late-onset retinal degeneration, and age-related macular degeneration have significant impact on human health and quality of life. Nine million Americans suffer progressive vision loss due to retinal neurodegenerative diseases. Retinitis pigmentosa affects one in four thousand individuals. It is the fourth leading cause of visual disability in the United States, after diabetic retinopathy, age-related macular degeneration, and glaucoma.

Age-related macular degeneration (AMD) is a neurodegenerative, neuroinflammatory disease of the macula, which is responsible for central vision loss. AMD is the leading cause of vision loss in people over age 65. Eight million people are legally blind from macular degeneration worldwide, and as the population ages this number is expected to grow The pathogenesis of age-related macular degeneration involves chronic neuroinflammation in the choroid (a blood vessel layer under the retina), the retinal pigment epithelium (RPE), a cell layer under the neurosensory retina, Bruch's membrane and the neurosensory retina, itself. The disease first manifests as a dry form that involves the accumulation of drusen—cell debris and inflammatory material that form small masses within the RPE and Bruch's membrane. Drusen contain broken down cell membranes and other cell fragments and are highly antigenic, activating a localized microglial and macrophage-mediated inflammatory response within the retina. Over time, the toxic mediators associated with this inflammation break down Bruch's membrane and the RPE and can lead directly to vision loss or may lead to the leakage of vascular endothelial-derived growth factor from the choroidal circulation into the subretinal space. This, in turn, can lead to the formation of abnormal blood vessels, called choroidal neovascularization. Since these blood vessels are abnormal, they often leak serum, causing retina exudates and can sometimes bleed. Since fluid is involved, this is called, "wet" age-related macular degeneration. The "wet" and "dry" forms of age-related macular degeneration can co-exist, both involving neuroinflammation.

The microglial-mediated pathology is also common to a variety of central nervous system neurodegenerative diseases including Alzheimer's disease, Parkinson's disease, amyotrophic lateral sclerosis, Huntington's disease, and acute spinal cord trauma. Brain injury is another cause of lifelong disability. For example, brain injury in the perinatal period can lead to cerebral palsy, which also involves microglial cells in the peri-ventricular leukomalacia following the injury.

There is a strong and immediate need in the art for clinically effective treatments for all these diseases, and inhibiting the common pathway of microglial-mediated tissue destruction as provided by the present disclosure meets this need.

SUMMARY OF THE INVENTION

A composition is provided comprising a nanoscale drug-nanoparticle formulation, wherein the formulation comprises at least one biologically active compound. The biologically active component is selected from the group consisting of natural steroids such as Cholesterol, Progestins Pregnenolone,17-hydroxypregnenolone, Progesterone, 17-hydroxyprogesterone, Androgens, Androstenedione, 4-hydroxy-Androstenedione11β-hydroxyandrostenedione, Androstanediol, Androsterone, Epiandrosterone, Adrenosterone, Dehydroepiandrosterone, Dehydroepiandrosterone Sulphate, Testosterone, Epitestosterone, 5α-dihydrotestosterone, 5β-dihydrotestosterone, 11β-hydroxytestosterone, 11-ketotestosterone, Estrogens, Estrone, Estradiol, Estriol, Corticosteroids, Corticosterone, Deoxycorticosterone, Cortisol, 11-Deoxycortisol, Cortisone, 18-hydroxycorticosterone, 1α-hydroxycorticosterone, Aldosterone, synthetic steroids, anti-inflammatory agents, vitamins, peptides, growth factors, CNS stimulants, oligonucleotides, siRNAs, microRNAs, resolvins, neurostimulants and protectants. The biologically active compound may be fluocinolone acetonide, ranibizumab, minocycline, rapamcyin, methyl prednisone, dexamethasone, insulin, estradiol, CNTF, vitamin A, vitamin C, vitamin E, an antioxidant and an oligonucleotide, or a pharmaceutically acceptable salt thereof.

In the composition, the size of the nanoparticle is equal to or less than about 1000 nm, less that about 500 nm, less than about 200 nm, less than about 150 nm, less than about 100 nm, less than about 90 nm, less than about 80 nm, less than about 70 nm, less than about 60 nm, less than about 50 nm, less than about 40 nm, less than about 30 nm, less than about 20 nm, less than about 19 nm, less than about 18 nm, less than about 17 nm, less than about 16 nm, less than about 15 nm, less than about 14 nm, less than about 13 nm, less than about 12 nm, less than about 11 nm, less than about 10 nm, less than about 5 nm, less than about 4 nm, less than about 3 nm, less than about 2 nm, less than about 1 nm, or any value there-between or less.

The nanoparticle of the composition may be a soft nanoparticle, such as a dendrimer-branched or star-branched polymer, or dendrimer-polymer hybrid. The dendrimer-branched polymer may consist of polyamidoamine (PAMAM), priostar, polyester, polyether, polylysine, or polyethylene glycol (PEG), polypeptide dendrimers. The star-branched polymer may be a PEG star. The soft nanoparticle may have a diameter of 1.5 nanometers to 14.5 nanometers. Also provided is a composition comprising a nanoscale drug-nanoparticle formulation, wherein the formulation comprises at least one biologically active compound and the drug is incorporated into a hyperbranched formulation through encapsulation, complexation, or covalent linkage. The linkage may comprise a spacer consisting of a peptide, glutaric acid, or PEG to link the drug and the polymer.

In certain embodiments, the drug-nanoparticle is incorporated in a larger scale entity incorporating the drug-hyperbranched polymer, wherein the larger-scale entity consists of a polymer matrix, a microparticle, a nanoparticle, a liposome, a microcapsule, a nanocapsule, or a controlled-release implant.

In some embodiments, the dendrimer-drug nanoconjugate can be delivered alone or incorporated into a topical preparation an implanted device coating, and implanted drug-delivery system, an injectable or implantable hydrogel or may be incorporated into a contact lens. This may be injected into the systemic circulation, may be delivered to the surface of the eye in the form of a contact lens, applied as an eyedrop or delivered into the corneal stroma. It may be applied to the subconjunctival space, the sub-tenons space, the episcleral space or intrasclerally. It may be delivered to the choroid, the suprachoroidal space, the sub-RPE space the sub-retinal space the epiretinal space, the intravitreal space or the anterior chamber.

In some embodiments, the nanoscale drug-hyperbranched polymer formulation is applied as a coating on an implantable device.

A composition is provided comprising a nanoscale drug-nanoparticle formulation, wherein the formulation comprises at least one biologically active compound, and wherein sustained release of the active compound occurs over a period of time. The release may occur over a period of minutes, hours, days, months, or years.

A composition is provided comprising a nanoscale drug-nanoparticle formulation, wherein the formulation comprises at least one biologically active compound, and wherein the composition provides sustained delivery of the compound to a targeted site in a patient. The targeted site may the vitreous of the eye, and the sustained delivery may over a period of seconds, minutes, hours, days, weeks, or months.

A composition is provided comprising at least one anti-inflammatory compound conjugated to a dendrimer, wherein the composition is encapsulated in a biodegradable particle selected from the group consisting of a PLA nanoparticle or a PGLA microparticle. The dendrimer may be PAMAM-G4-OH and the anti-inflammatory compound may be selected from the group consisting of natural or synthetic steroids or steroid analogs such as fluocinolone acetonide, methyl prednisone or dexamethasone, an antioxidant, an antibiotic such as minocycline, an immunomodulator or an immunosupressant.

A method of treatment of a neuroinflammation-related disorder is provided, comprising administering a composition comprising a nanoscale drug-nanoparticle formulation, wherein the formulation comprises at least one biologically active compound, and wherein said neuroinflammation-related disorder is a disease of the retina, optic nerve, central nervous system, the spinal cord or the peripheral nervous system. The disease may be selected from the group consisting of retinitis pigmentosa, age-related macular degeneration, cerebral palsy optic neuritis, blunt and penetrating injuries, infections, sarcoid, sickle cell disease, retinal detachment, temporal arteritis, retinal ischemia, arteriosclerotic retinopathy, hypertensive retinopathy, retinal artery blockage, retinal vein blockage, hypotension, diabetic retinopathy, macular edema, stroke, uveitis, photoreceptor degeneration, autoimmune retinopathy, inherited photoreceptor degeneration, myopic retinal degeneration, retinal pigment epithelial degeneration, diabetic retinopathy, central serous retinopathy, acute zonal outer occult retinopathy, acute multifocal placoid pigment epitheliopathy, multiple evanescent white dot syndrome, cancer associated retinopathy, retinal vasculitis, Alzheimer's disease, Parkinson's disease, brain or spinal cord trauma, AIDS dementia, age-related loss of cognitive function, memory loss, amyotrophic lateral sclerosis, seizure disorders, alcoholism, aging, and neuronal loss.

Also provided is a method of treating progressive vision loss in a human in need thereof, the method comprising administering to the eye of said human a composition of comprising a nanoscale drug-nanoparticle formulation, wherein the formulation comprises at least one biologically active compound. The progressive vision loss may be associated with at least one condition selected from the group consisting of uveitis, age-related macular degeneration, diabetic retinopathy, and retinitis pigmentosa. Further provided is a method of treating ocular neuroinflammation in a human in need thereof. The administering may occur once, or may occur two or more times over a period of days, weeks or months.

Further provided is a medical device comprising a nanoscale drug-nanoparticle formulation, wherein the formulation comprises at least one biologically active compound, and instructions for administering the composition.

BRIEF DESCRIPTION OF THE FIGURES

FIGS. 2A-2F are a series of photographs showing retinal biodistribution of free-FITC and dendrimer-conjugated FITC (D-FITC) in healthy Sprague-Dawley (SD) and Royal College of Surgeons (RCS) retinal degeneration model rats with active neuroinflammation. Epi-fluorescence histology from retinal cryosections performed 24-hours and 10-days after intravitreal injection shows (FIG. 2A) D-FITC distribution in normal SD rats at 24-hours; (FIG. 2B) D-FITC distribution in the RCS retinal neurodegeneration model at 24-hours; (FIG. 2C) D-FITC retained within areas of neuroinflammation at 10-days; (FIG. 2D) Free-FITC distribution in SD at 24-hours; (FIG. 2E) Free-FITC uniformly distributed in the RCS rat retina at 24-hours; and (FIG. 2F) Free-FITC cleared from the retina in RCS rats 10-days after injection.

FIGS. 3A and 3B are bar graphs. (FIG. 3A) Mean ERG b-wave amplitudes in 9-week RCS rats, four-weeks after a single 1 µl right-eye injection of 1 µg or 3 µg dendrimer-FA (D-FA) or unconjugated, free-FA. There is significant preservation of the ERG amplitude with dendrimer-FA treatment when compared to treatment with FA alone or the control untreated rats. (FIG. 3B) Outer Nuclear Layer cell densities in the same 9-week RCS rats with data from 0.2 µg/day and 0.5 µg/day IDDIs.

(FIG. 5A) Dendrimer-FITC (D-FITC) distribution in Sprague-Dawley (SD) retina; (FIG. 5B) D-FITC distribution in RCS rat retina; (FIG. 5C) unconjugated FITC distribution in SD; (FIG. 5D) PLGA-D-FITC microspheres in SD.

FIG. 7 is a bar graph showing microglia counts within the outer debris zone in the retina of nine week-old control rats and rats given different doses of fluocinolone acetonide.

FIGS. 8A-8F show a decrease in the [$^{11}$C] PK11195 uptake from the first ten minutes to the last ten minutes (similar to control pups) is seen in the postnatal day 5 pup exposed to endotoxin in utero that was treated with minocycline 15 mg/kg for three days suggestive of a decrease in activated microglial cells. An increase in the PK11195 uptake is noted in the untreated endotoxin exposed pup in the last ten minutes when compared to the first ten minutes suggestive of continued presence of activated microglial cells in the untreated endotoxin pups. This indicates that minocycline treatment has resulted in inhibition of activated microglial cells in the endotoxin exposed pup.

(FIG. 10A) D-FITC distribution in normal SD rats at 24-hours. (FIG. 10B) D-FITC distribution in the RCS retinal neurodegeneration model at 24-hours. (FIG. 10C), D-FITC (RCS) at ten days; (FIG. 10D), Free-FITC (SD) at 24 hours; (FIG. 10E), Free-FITC (RCS) at 24 hours; and (FIG. 10F), Free-FITC (RCS) at ten days.

FIGS. 11A-11D show microglial uptake of D-FITC. (FIG. 11A) ED-1 immuno-histochemical labeling of inner-retinal microglial cells; (FIG. 11B) D-FITC uptake within inner retinal microglia (60×); (FIG. 11C) outer retinal ED-1 labeled activated microglia; and (FIG. 11D) D-FITC uptake within activated microglia.

FIG. 12A shows glial-acidic fibrillary protein (GFAP) immunostaining of activated retinal astrocytes. FIG. 12B shows dendrimer-FITC uptake by activated retinal astrocytes.

FIG. 13A shows GFAP labeling of activated retinal Mueller cells in 5-week RCS rats (lateral view). FIG. 13B shows D-FITC uptake by activated retinal Mueller cells (same field as in FIG. 13A). D-FITC uptake within the retinal capillary is shown by the arrow. FIG. 13C shows GFAP labeling of retinal Mueller cells (axial view) at inner nuclear layer. FIG. 13D shows D-FITC uptake by retinal Mueller cells (axial view).

FIG. 14 is a photograph that shows uptake of D-FITC by retinal photoreceptors in 5-week RCS rats.

FIGS. 15A and 15B show D-FITC uptake by retinal capillaries. (FIG. 15A) lateral view and (FIG. 15B) lateral view with view of vessel cross-section.

FIGS. 16A and 16B are photographs showing inner retinal nanoparticle biodistribution in S334-ter-4 rats, seventy two hours after intravitreal injection. Green: FITC-labeled PS nanoparticles, Red: Rhodamine GFAP. (FIG. 16A) 50 nm FITC nanoparticles are seen within astrocyte somata. (FIG. 16B) 200 nm FITC nanoparticles remain confined to the pre-retinal vitreous, and do not appear to be taken into the cells that take up the dendrimer.

DETAILED DESCRIPTION OF THE INVENTION

Figures 1A, 1B, 1C, 1D:
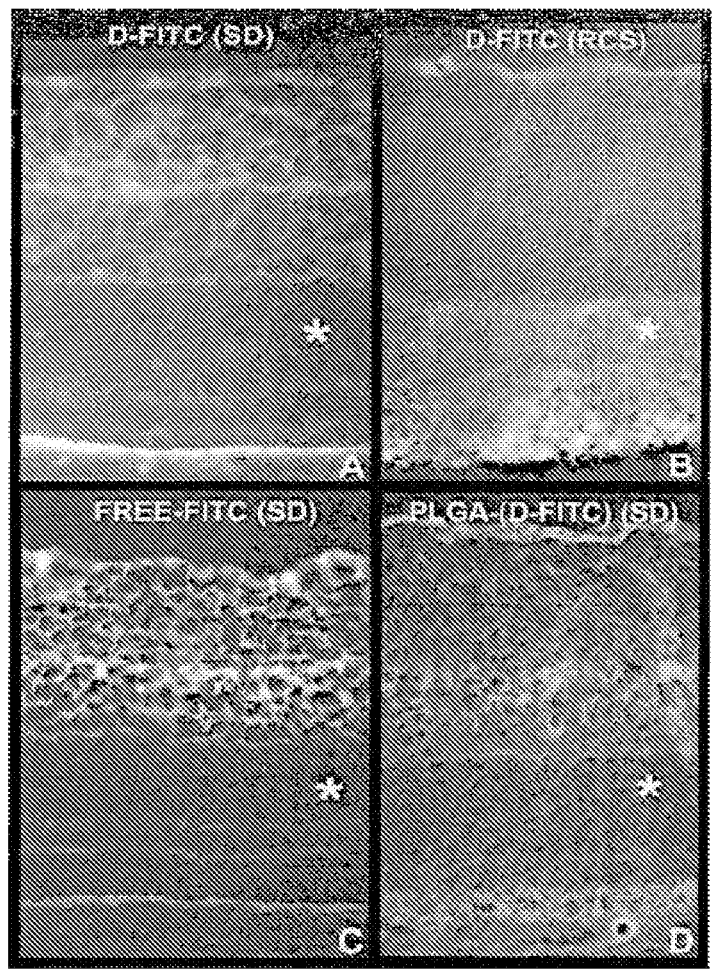
FIGS. 1A-1D show microglial cell uptake of dendrimers by flow cytometry. Control cells are indicated and compared with cellular uptake of dendrimers having different functional groups (COOH, $NH_2$, and OH).

Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

Introduction. Many effective pharmaceutical products and drugs fail to reach target tissue, or fail to remain in the target area, for long enough to achieve clinical effectiveness. One example is the synthetic corticosteroid fluocinolone acetonide for severe uveitis. Uveitis refers to inflammation or swelling of the eye's structures responsible for its blood supply. These structures are collectively known as the uveal tract, and include the iris, ciliary body, and choroids. Uveitis is classified by the structures it affects, the underlying cause, and whether it is chronic (longer than six weeks), or acute in nature.

Implants for sustained intravitreal delivery of fluocinolone acetonide are FDA-approved for patients with uveitis. However, drawbacks of these implants include multiple incisional procedures for the surgical implantation, a fifty percent incidence of glaucoma, and the non-erodible character of the implants. Another exemplary drug is the anti-inflammatory agent minocyline, which has potential for treating neuroinflammation in the retina and brain.

One underlying goal of the present disclosure is to provide new materials and methods for reducing microglia and glial activation to a cytotoxic and/or phagocytic phenotype associated with neuroinflammation. Such activation is common to a variety of diseases, and by reducing it, the associated destruction of bystander normal tissue can be decreased or eliminated. By doing so, the pathological manifestations of the tissue damage can be significantly reduced, leading to reduced clinical severity of disease, and improved health and quality of life. Any disease in which activated microglia, glia or the infiltration of systemic macrophages play a role is amenable to treatment described herein. In addition, the present invention can address the role that blood vessels play in neuroinflammatory diseases. The examples of diseases described herein are not intended to be limiting, nor are the drugs and pharmaceutical compositions intended to be limiting.

One suitable disease is age-related macular degeneration (AMD). AMD is classified as either wet (neovascular) or dry (non-neovascular). About 10% of patients who suffer from macular degeneration have wet AMD. This type occurs when new vessels form to improve the blood supply to oxygen-deprived retinal tissue. However, the new vessels are very delicate and break easily, causing bleeding and damage to surrounding tissue. The dry type is much more common and is characterized by drusen and loss of pigment in the retina. Drusen are small, yellowish deposits that form within the layers of the retina. These contain antigenic material that can activate retinal neuroinflammation.

Another disease is diabetic retinopathy, which refers to the effect of diabetes on the eye. People with diabetes may develop eye problems such as cataracts and glaucoma, but the disease's effect on the retina is the main cause of vision loss. Over time, diabetes affects the circulatory system of the retina. The earliest phase of the disease is known as background diabetic retinopathy. In this phase, the arteries in the retina become weakened and leak, forming small, dot-like hemorrhages. These leaking vessels can lead to swelling or edema in the retina, causing decreased vision.

Proliferative diabetic retinopathy can follow, in which circulatory problems cause areas of the retina to become oxygen-deprived or ischemic. New, fragile, vessels develop as the circulatory system attempts to maintain adequate oxygen levels within the retina. This phase is called neovascularization and is characterized by delicate vessels that hemorrhage easily. Blood may leak into the retina and vitreous, causing spots or floaters, along with decreased vision. As the disease progresses, continued abnormal vessel growth and scar tissue may cause worsening problems such as retinal detachment and glaucoma. Thus, it is important to control and prevent the neovascularization and thereby eliminate the blood leakage. By virtue of their biodistribution, dendrimers can target and treat neuroinflammatory changes in blood vessels by delivering therapeutic molecules.

Retinitis pigmentosa (RP) refers to a rare, hereditary disease that causes the rod photoreceptors in the retina to undergo gradual degeneration. The disease may be X-linked (passed from a mother to her son), autosomal recessive (genes required from both parents) or autosomal dominant (gene required from one parent) trait. Since it is often a sex-linked disease, retinitis pigmentosa affects males more than females. The course of RP varies. For some people, the affect on vision may be mild. In others disease can progress to blindness.

To aid in describing the present methods of treatment, the following terms associated with eye structure and function are used. The "retina" is a multi-layered sensory tissue that lines the back of the eye. It contains millions of photoreceptors that capture light rays and convert them into electrical impulses. These impulses travel along the optic nerve to the brain where they are turned into images. There are two types of photoreceptors in the retina: rods and cones. The retina contains approximately six million cones. The cones are contained in the macula, the portion of the retina responsible for central vision. They are most densely packed within the fovea, the very center portion of the macula. Cones function best in bright light and allow color recognition.

The "vitreous" is a thick, transparent substance that fills the center of the eye. It is composed mainly of water and comprises about two thirds of the eye's volume, giving it form and shape. The viscous properties of the vitreous allow the eye to return to its normal shape if compressed. In children, the vitreous has a consistency similar to an egg white. With age it gradually thins and becomes more liquid. The vitreous is firmly attached to certain areas of the retina. As the vitreous thins, it separates from the retina, often causing floaters.

The vitreous is within the posterior segment of the eye, and is one route for administering drugs that target abnormal blood vessel growth that characterizes several of the diseases discussed herein. For example, an antibody fragment (ranibizumab) directed to human vascular endothelial growth factor A (VEGF-A) is injected into the vitreous portion once a month. However, the injection procedure itself can cause serious adverse events such as inflammation of the interior of the eye, retinal detachment, retinal tear, and other problems. Thus, a treatment that requires fewer injections or administration procedures would be likely to decrease unwanted and traumatic adverse effects.

The "ciliary body" is located near the front of the eye, above and below the lens. It is targeted by drugs for treating glaucoma. It produces aqueous humor, so lowering aqueous humor production causes a decrease in the intraocular pressure.

Thus, depending on the location of the pathological event, such as overproduction of aqueous humor, growth of abnormal blood vessels, or unwanted activation of neuroinflammatory cells in the retina, the drug administration according to the present methods and compositions can be tailored to target the specific cells and tissues. Routes of administration to the eye have been studied and described, for example in Lee, T. W. et al., *J. Ocular Pharm.* 20:43-53 and 55-64 (2004). Such routes of administration will be within the skill of the medical professionals by whom the present methods and compositions will be practiced.

Other related conditions and/or diseases that can be treated with particular embodiments disclosed herein include such conditions relating to neuroinflammation, and/or inflammation of the eye, including but not limited to: retinitis pigmentosa, macular degeneration, cerebral palsy, optic neuritis, blunt and penetrating injuries, infections, sarcoid, sickle cell disease, retinal detachment, temporal arteritis, retinal ischemia, arteriosclerotic retinopathy, hypertensive retinopathy, retinal artery blockage, retinal vein blockage, hypotension, diabetic retinopathy, macular edema, stroke, Alzheimer's disease, Parkinson's disease, brain or spinal cord trauma, AIDS dementia, age-related loss of cognitive function, memory loss, amyotrophic lateral sclerosis, seizure disorders, alcoholism, aging, and neuronal loss.

Microglia. Microglia are resident members of the dendritic immune system within the retina and central nervous system (CNS) and are activated by many stimuli, including bacterial cell wall lipopolysaccharides and gangliosides within damaged lipid membranes. (Jou, I. et al., *The American Journal of Pathology* 2006; 168:1619-1630; Min, K. J. et al., *Glia* 2004; 48:197-206; Pyo, H. et al., *The Journal of Biological Chemistry* 1999; 274:34584-34589.)

In the case of eye disease, damaged photoreceptor cell membranes provide one antigenic stimulus for microglial activation. Upon activation, microglia assume a phagocytic phenotype, migrate towards the degenerating photoreceptors, and scavenge the debris. In addition, activated microglia orchestrate the recruitment and activation of other microglia via chemotactic cytokines such as CCL-5 (RANTES), macrophage inflammatory proteins (MIP-1α and MIP-1β), macrophage chemoattractant proteins MCP-1 and MCP-3.

After assuming the activated phenotype, microglia release cytotoxic free-radicals such as NO and superoxide anion as well as proinflammatory cytokines such as TNF-α, IL-1 and IL-6 incurring further photoreceptor cell damage (bystander lysis). Undampened, this induces a positive feedback cycle of microglia-mediated photoreceptor cell death which in turn exacerbates the bystander lysis of additional photoreceptors, thus coupling of photoreceptor apoptosis and necrosis, accelerating disease progression.

Microglial cells constitute about 10-20% of the cells in the adult brain and form part of the normal surveillance systems in the central nervous system. Microglial cells are known to be activated by stimuli such as trauma, infection, inflammation and ischemia. As a result of these stimuli, there is upregulation of a number of cell adhesion markers along with secretion of pro-inflammatory mediators, generation of reactive oxygen species and peroxynitrites that may lead to further neuronal damage. (Zeng, H. Y. et al., *Invest. Ophthalmol. Vis Sci.* 46:2992-2999, 2005; Bell, M. J. et al., *J. Neurosci. Res.* 70:570-579, 2002.)

One goal for treating neuroinflammatory diseases of the eye is to target drugs to the posterior segment of the eye. With aging, the retinal pigment epithelium (RPE) can sometimes lose its ability to process waste products produced by the photoreceptor cells. Deposits of this waste, called drusen, can distort and damage the retina leading to an eye condition called dry macular degeneration. Other potential sites for targeting drugs in the eye include blood vessels, neuroinflammatory cells, retinal pigment epithelium, optic nerve, cornea, iris, lens and the ciliary body.

The continued persistence of eye disease associated with microglial activation is evidence of the need for new treatments, and an important parameter for introducing a new treatment is its comparison to existing therapeutics. There have been attempts to introduce drugs using sustained release formulations, but none have achieved widespread success.

In the case of nanoparticles, the particle size affects intravitreal kinetics. Fluorescence-labeled-polystyrene micro and nanospheres (2 μm, 200 nm and 50 nm in diameter) were observed in the vitreous cavity of rabbits for over 1 month (Eiji Sakurai, H. O. et al., *Ophthalmic Research* 33:31-36 (2001)). Histological studies using a fluorescence microscope revealed that 2 μm diameter particles were seen in the vitreous cavity and trabecular meshwork, while nanospheres with a diameter of smaller than 200 nm were also observed in the retina as well as the tissues (Eiji Sakurai, H. O. et al., *Ophthalmic Research* 33:31-36 (2001)).

Bourges et al. reported studies of ocular drug delivery targeting the retina and retinal pigment epithelium using polylactide (PLA) nanoparticles (NP) (Jean-Louis Bourges, S. E. G. et al., *Investigative Opthalmology & Visual Science* 44:3562-3569 (2003)). The kinetics and localization of polylactide (PLA) nanoparticle within the intraocular tissues were studied. A single intravitreous injection (5 μl) of the NP suspension (2.2 mg/ml) encapsulating Rh-6G (fluorescent molecule) was performed on Lewis rats. The PLA NPs caused no adverse toxicity effects, and preferentially localized in the RPE cells. Encapsulated Rh-6G diffuses from the NPs and stains neuroretina and RPE cells. This suggested that specific targeting of these tissues is feasible. NPs were found within the RPE cells for four months after a single injection (Jean-Louis Bourges, S. E. G. et al., *Investigative Opthalmology & Visual Science* 44(8):3562-3569 (2003)). This result shows steady and continuous delivery of drugs can be achieved to RPE cells. If the NP size is small (≈<200 nm), they may be taken in by the RPEs, and if the size is ≈>2 μm, then they may stay in the vitreous chamber to a large extent.

At present, there are no effective treatments for RP and atrophic (dry) ARMD. Clinical studies have identified that the oral antioxidant, vitamin A palmitate 15,000 IU/d, slows the progression of ERG loss in patients with retinitis pigmentosa (Berson, E. L. et al. *Arch Ophthalmol* 111(11): 1456-9 (1993)). The Age-Related Eye Disease Study further identified that beta-carotene, vitamin E, vitamin C, zinc and copper taken orally, reduced the risk for patients with high-risk features of atrophic-ARMD of progressing to the neovascular form by approximately 25% (AREDS Study Group, 2001). In addition, a phase II clinical trial of ciliary-derived neurotrophic factor has been reported. This molecule has strong anti-apoptotic effects. In RP animal models that received the drug, photoreceptor degeneration was slowed, but ERG amplitudes were not preserved (Liang, F. Q. et al. *Mol Ther* 4(5):461-72 (2001); Tao, W. et al., *Invest Ophthalmol Vis Sci* 43(10):3292-8 (2002); Sieving, P. A. et al., *Proc Natl Acad Sci USA* 103(10):3896-901 (2006); Tao, W., *Expert Opin Biol Ther* 6(7):717-26 (2006); Zeiss, C. J. et al., *Exp Eye Res* 82(3):395-404 (2006)).

Steroids, including natural and synthetic glucocorticoids have been shown to exhibit neuroprotective properties through a number of mechanisms: 1) they intercalate within lipid membranes, mechanically stabilizing them (Ignarro, L. J., *J Pharmacol Exp Ther* 182(1):179-88 (1972); Horwitz, L. D. et al., *Free Radic Biol Med* 21(6):743-53 (1996); Wang, Y. et al., *J Pharmacol Exp Ther* 277(2):714-20 (1996)); 2) as antioxidants, they inhibit lipid peroxidation (Eversole, R. R., et al. *Circ Shock* 40(2):125-31 (1993); Horwitz, L. D., et al. *Free Radic Biol Med* 21(6):743-53 (1996); Letteron, P., et al. *Am J Physiol* 272(5 Pt 1):G1141-50 (1997)); 3) they inhibit AP-1 (a pro-apoptotic signaling molecule) (Gonzalez, M. V., et al. *J Cell Biol* 150(5):1199-208 (2000); Wenzel, A., et al. *Invest Ophthalmol Vis Sci* 42(7):1653-9 (2001)); and 4) through their potent anti-inflammatory effects, they suppress microglial activation and their ability to produce major histocompatibility complex (MHC) antigens, NO and TNF-alpha (Kiefer, R., et al., *J Neuroimmunol* 34(2-3):99-108 (1991); Hall 1993; Lehmann, C., et al. *Crit Care Med* 27(6):1164-7 (1999); Chang, J., et al. *Nuerochem Res* 25(7): 903-8 (2000); Drew, P. D. et al., *Brain Res Bull* 52(5):391-6 (2000); Dinkel, K. et al., *J Neurochem* 84(4):705-16 (2003); Lieb, K. et al., *Neurochem Int* 42(2):131-7 (2003); Glezer, I. et al., *Neuroscientist* 10(6):538-52 (2004)).

The neuroprotective, anti-apoptotic effects of antioxidants have been demonstrated in photoreceptors in a number of studies (Carmody, R. J. et al., *Exp Cell Res* 248(2):520-30 (1999); Sanvicens, N. et al., *J Biol Chem* 279(38):39268-78 (2004); Tanito, M. et al. *J Neurosci* 25(9):2396-404 (2005)). Some glucocorticoid and non-glucocorticoid steroids exert anti-oxidant effects and are neuroprotective in acute and chronic retinal neurodegeneration models (Behl, C. et al., *Mol Pharmacol* 51(4):535-41 (1997); Wenzel, A. et al., *Invest Ophthalmol Vis Sci* 42(7):1653-9 (2001); Dykens, J. A. et al., *Biochem Pharmacol* 68(10):1971-84 (2004)). Estrogens have been shown to be neuroprotective against oxidative stressors in vitro and in vivo in transgenic RP animal models (Dykens, J. A. et al., *Biochem Pharmacol* 68(10):1971-84 (2004); Sanvicens, N. et al., *J Biol Chem* 279(38):39268-78 (2004)).

Glucocorticoids were found to inhibit Fas, which is a main apoptosis mediator in circulating immunologic cells, such as T lymphocytes and neutrophils, by specific down-regulation of Fas gene expression (Cox, G. *J. Immunol.* 154(9):4719-25.1995; Yang, Y. et al., *J. Exp. Med.* 181: 1673-82, 1995; Chang, L. C. et al., *J. Endocrinol.* 183:569-83.2004). The capacity of steroids to bind to free radicals was shown in trauma-associated spinal cord neural cell degeneration in humans (Hall 1993) and in oxidative stress-damaged uveal tissue in a Wistar rat model of chronic uveitis (Augustin, A. J. et al., *Br J Ophthalmol* 80(5):451-7, 1996). Intravitreal injections of triamcinolone in albino rabbits (Dierks, Lei et al., *Arch. Ophthalmol.* 123(11):1563-9 2005) enhanced ERG thresholds and were associated with improved retinal morphology.

Glucocorticoid receptors were also localized in apoptotic photoreceptor cells of mouse degenerating retina and can be activated in response to intraocular injection of dexamethasone. Once activated, they inhibit an activator protein (AP)-1 and reduce apoptotic reactions. In dexamethasone-treated eyes, a morphological preservation of retinal outer nuclear cell layer was observed (Wenzel, A. et al., *Invest Ophthalmol Vis. Sci.* 42(7):1653-9 (2001)).

The reports discussed above confirm the need for more effective treatments of these diseases and conditions. Such treatments are provided by the compositions and methods disclosed herein.

Nanodevices and Nanosystems. As used herein, "nanodevices" and/or "nanosystems" may be used interchangeably, and may refer to microparticles or nanoparticles comprising dendrimers and at least one other therapeutic agent.

As used herein, the term "microparticle" or "microparticle system" generally refers to microparticles or microcapsules having a diameter of approximately less than 1 nm to approximately 2,000 nm with a diameter of preferably between 100-500 nm. Further, "nanoparticles" typically have a diameter range of from less than 1 nm to 1000 nm. As provided herein, certain embodiments of the present invention relate to a series of biocompatible nanoparticle formulations in the form of nanodevices that can be used, for example, as drug delivery vehicles that have been designed to retain and/or deliver drugs or other therapeutic agents over an extended period of time. These formulations permit modification to a desirable size, provide adequate mechanical strength and exhibit exceptional permeability and surface characteristics. Thus, the formulations may contain polymer matrices, liposomes, microcapsules, nanocapsules, controlled-release implants, and the like. A preferred nanoparticle is a soft nanoparticle.

In certain particular embodiments, the nanodevices described herein allow for a single dose of the therapeutic agent to the subject, on other embodiments, the nanodevices allow for multiple doses administered to a subject, preferably over an extended period of time. In certain embodiments, the nanodevices allow for a controlled-release of at least one therapeutic agent over a period of at least several hours, at least several days, at least several weeks, or at least several months.

One advantage conferred by the present invention relates to improved control of the permeability of the particles and the release rate of drug conjugated or adsorbed to the nanoparticle periphery. Generally, the nanodevices comprise dendrimers, which may be formed from a variety of materials, including synthetic polymers and biopolymers (e.g., proteins and polysaccharides) and can be used as carriers for other drugs and biotechnology products, such as growth factors and genes or may be used to carry imaging agents. These nanodevices may comprise a polymeric core shell, into which a pharmaceutical drug or other therapeutic agent may be incorporated by way of chemical and/or physical linking or attachment by way of adsorption or chemical conjugation. Alternatively, the therapeutic agent may be conjugated to a polymer within the nanoparticle core. Non-charged small drugs may be attached to larger molecules, preferably charged polymers.

Prior to using the nanoparticles (comprising dendrimers), the particles may be cryoprotected or lyphilized to extend the therapeutic life of the nanoparticle. Cryoprotecting the nanoparticles, with concomitant stabilization, is provided by means of lyophilization. The washed particles are then suspended in cryoprotective solution and lyophilization of the suspension is performed in a suitable lyophilization apparatus.

Dendrimers. According to the present disclosure, pharmaceutical drug compositions are administered to the eye in a nanodevice comprising polymeric material to which the drug is associated or conjugated. In one embodiment, the polymeric material is in the form of dendrimers, which are manufactured to have a high degree of molecular uniformity, narrow molecular weight distribution, specific size and shape characteristics, and a highly-functionalized terminal surface. For example, ethylenediamine-core poly (amidoamine) (referred to as "PAMAM") dendrimers represent a class of macromolecular architecture called "dense star" polymers. In some embodiments, the dendrimer is a partially acetylated generation 4 or 5 (G4 or G5, respectively) poly-amideamine (PAMAM) or polypropylamine (POPAM) dendrimer.

Unlike classical polymers, these dendrimers are manufactured in a series of repetitive steps starting with a central initiator core. Each subsequent growth step represents a new "generation" of polymer with a larger molecular diameter, twice the number of reactive surface sites, and approximately double the molecular weight of the preceding generation. The dendrimer-drug nanodevices can themselves be further packaged for enhanced sustained release. For example, they can be encapsulated into biodegradable poly(lactide-co-glycolide) (PLGA) microspheres as described in more detail herein and in the Examples.

Typically, dendrimer molecules have diameters ranging from 1.5 nanometers to 14.5 nanometers, such as 3 to 10 nanometers, which is comparable to the size of small proteins. They have a highly branched, three dimensional architecture, with high functionality and very low polydispersity (defined as the distribution of individual molecular weights in a batch of polymers). In view of these characteristics, they are capable of carrying many molecules such as pharmaceutical agents, and of possessing homogeneous size, making them suitable for specific modes of administration, such as intraocular.

The pharmaceutical agent of interest can be attached to the dendrimer through a permanent or cleavable bond, or physically encased inside the core of the dendrimer micelle. The dendrimer backbone can also have functional sites for incorporating targeting moieties to facilitate delivery to the desired biological site. The functional sites can also allow for modifying the dendrimer backbone, for example to increase the hydrophilicity and solubility in aqueous media, or to increase solubility in lipid regions.

Advantages of dendrimers include maintenance of drug levels at therapeutically desirable ranges; reducing or minimizing unwanted side effects; decreasing the amount of drug that has to be administered; decreased number of doses, and in the case of ocular administration, less invasive forms of dosing; and enhancing the administration of drugs that have short half-lives. Some or all of these advantages come into play in the various compositions and methods disclosed herein.

Dendrimers are prepared according to known methods. For example, U.S. Pat. No. 5,714,166, provides methods for preparing dendrimers having a variety of sizes and compositions. Yang, H. et al., *J. Biomater. Sci. Polymer Edn.* 17:3-19 (2006) reviewed methods for associating therapeutic agents with dendrimers of the PAMAM compositions. The agent can be entrapped within the dendritic "box" which consists of a densely packed shell on the dendrimer surface. PEGylated dendrimers are useful for holding agents in a hydrophobic core and increasing the water solubility of hydrophobic agents. Dendrimer-drug conjugates can be prepared in which the drug is conjugated to the dendrimer surface, or to PEG which itself is attached to the dendrimer surface.

In the Examples described herein, PAMAM-G4-OH dendrimers were conjugated to fluocinolone acetonide (FA) for injection into the eye. The dendrimer administration of the drug offered advantages over the drug alone. A six-fold lower total FA dose gave greater functional and neuroprotective efficacy than sustained release FA alone, confirming that it is possible to administer less drug when conjugated to dendrimer, yet achieve the same or greater therapeutic effects. Once the dendrimer-FA was taken into the cells, it was unavailable for entering the systemic circulation in the short term, offering another advantage over free drug. Fellow-eye cross-over effects were lower in the dendrimer-FA treated eyes than free FA, which was also attributed to the enhanced cellular uptake of the dendrimer-FA conjugates.

Dendrimers suitable for the present methods and compositions are commercially available. For example, PAMAM dendrimers are available (Aldrich) having specific molecular weight, diameter, and surface groups, depending on the generation. In some Examples herein, PAMAM-G4-OH (fourth generation dendrimers with —OH terminal groups) were obtained from Aldrich. The choice of dendrimers will depend on several factors, including but not limited to: the route of administration, the target tissue, type of pharmaceutical drug utilized, the disease or condition to be treated, the overall health of the subject, the pharmaceutical drug formulation, and others.

"Associated with" means that the drug or pharmaceutical agent, or the imaging or targeting agent (collectively referred to as "agent") can be physically encapsulated or entrapped within the core of the dendrimer, dispersed partially or fully throughout the dendrimer, or attached or linked to the dendrimer or any combination thereof, whereby the attachment or linkage is by means of covalent bonding, hydrogen bonding, adsorption, absorption, metallic bonding, van der Waals forces or ionic bonding, or any combination thereof.

The association of the agent and the dendrimer may optionally employ linkers, connectors and/or spacers to facilitate the preparation or use of the dendrimer conjugates. Suitable connecting groups are groups which link a targeting director to the dendrimer without significantly impairing the effectiveness of the director or the effectiveness of any other agent present in the dendrimer conjugate. These connecting groups may be cleavable or non-cleavable and are typically used in order to avoid steric hindrance between the target director and the dendrimer. Since the size, shape and functional group density of the dendrimers can be rigorously controlled, there are many ways in which the carried material can be associated with the dendrimer.

For example, (a) there can be covalent, coloumbic, hydrophobic, or chelation type association between the agent(s) and entities, typically functional groups, located at or near the surface of the dendrimer; (b) there can be covalent, coulombic, hydrophobic, or chelation type association between the agent(s) and moieties located within the interior of the dendrimer; (c) the dendrimer can be prepared with an interior which is predominantly hollow, allowing for entrapment (e.g., physically within or by association with the interior moieties of the dendrimer) of the agent(s) within the interior (void volume), (e.g., magnetic or paramagnetic cores or domains created by the chelation and reduction of metal ions to the zero valence state within the dendrimer).

Dendrimers containing magnetic interiors can be used for harvesting various bioactive entities that can be complexed with various dendrimer surfaces by use of magnets and the like, wherein the release of the carried material can optionally be controlled by congesting the surface of the dendrimer with diffusion controlling moieties; or (d) various combinations of the aforementioned options can be employed. Dendrimers useful in the present methods and compositions include the dense star polymers described in U.S. Pat. Nos. 4,507,466, 4,558,120, 4,568,737 or 4,587,329.

The pharmaceutical agents which are suitable for use in the dendrimer conjugates include any materials for in vivo, ex vivo or in vitro use for diagnostic or therapeutic treatment of mammals which can be associated with the dendrimers without appreciably disturbing the physical integrity of the dendrimer, for example, but not limited to fluocinolone acetonide, minocycline, a chemotherapeutic agent, an anti-oncogenic agent, an anti-angiogenic agent, a tumor suppressor agent, an anti-microbial agent, a nucleic acid (including RNA, DNA, cDNA, siRNA, microRNA, and chemical or synthetic nucleic acid analogs), a protein, a polypeptide, a peptide, an amino acid (including naturally occurring and/or artificial amino acids or analogs), a vitamin, a mineral, a growth factor (such as epidermal growth factor, ciliary neurotrophic growth factor, TGF-beta, bone morphogenic protein, fibroblast growth factor, neurotrophins (NGF, BDNF, NT3, etc.), granulocyte-colony stimulating factor, granulocyte-macrophage colony stimulating factor, platelet-derived growth factor, erythropoietin, thrombopoietin, myostatin, growth differentiation factor 9, basic fibroblast growth factor, epidermal growth factor, hepatocyte growth factor, and others), an angiogenic factor (such as matrix metalloproteinases, vascular endothelial growth factor, angiopoeitins, Notch family members, Delta-like ligands, etc.), integrins, an apoptotic factor, a cytokine, or an expression construct comprising a nucleic acid encoding a therapeutic protein, although the present invention is not limited by the nature of the therapeutic agent. It will be appreciated by the skilled artisan that proactive factors may be countered by anti-active factors (such as siRNA, micro RNA, antisense, inhibiting antibodies, etc.) and these factors are also considered as part of the instant disclosure.

In further embodiments, the therapeutic agent is protected with a protecting group selected from photo-labile, radio-labile, and enzyme-labile protecting groups. In some embodiments, the chemotherapeutic agent is selected from a group consisting of, but not limited to, platinum complex, verapamil, podophylltoxin, carboplatin, procarbazine, mechloroethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, bleomycin, etoposide, tamoxifen, paclitaxel, taxol, transplatinum, 5-fluorouracil, vincristin, vinblastin, and methotrexate. In some embodiments, the anti-oncogenic agent comprises an antisense nucleic acid (e.g., RNA, molecule). In certain embodiments, the antisense nucleic acid comprises a sequence complementary to an RNA of an oncogene. In preferred embodiments, the oncogene includes, but is not limited to, abl, Bcl-2, Bcl-xL, erb, fms, gsp, hst, jun, myc, neu, raf; ras, ret, src, or trk. In some embodiments, the nucleic acid encoding a therapeutic protein encodes a factor including, but not limited to, a tumor suppressor, cytokine, receptor, inducer of apoptosis, or differentiating agent. In preferred embodiments, the tumor suppressor includes, but is not limited to, BRCA1, BRCA2, C-CAM, p16, p21, p53, p73, Rb, and p27. In preferred embodiments, the cytokine includes, but is not limited to, GMCSF, IL-1, IL-2, IL-3, IL-4, IL-5, IL-6, IL-7, IL-8, IL-9, IL-10, IL-11, IL-12, IL-13, IL-14, IL-15, IFN-beta, IFN-gamma, and TNF. In certain embodiments, the inducer of apoptosis includes, but is not limited to, AdE1 B, Bad, Bak, Bax, Bid, Bik, Bim, Harakid, and ICE-CED3 protease. In some embodiments, the therapeutic agent comprises a short-half life radioisotope.}}

In some embodiments of the present invention, the nanodevice further comprises an imaging agent comprising a radioactive label including, but not limited to $^{14}C$, $^{36}Cl$, $^{57}Co$, $^{58}Co$, $^{51}Cr$, $^{125}I$, $^{131}I$, $^{111}Ln$, $^{152}Eu$, $^{59}Fe$, $^{67}Ga$, $^{32}P$, $^{186}Re$, $^{35}S$, $^{75}Se$, $^{175}Yb$. In some embodiments, the imaging agent comprises a fluorescing entity. In a preferred embodiment, the imaging agent is fluorescein isothiocyanate.

For treatment of the wet form of macular degeneration, any of the currently available therapeutic agents are amenable to administration using the dendrimer conjugates herein, including Macugen® (pegaptanib sodium injection); ranibizumab, bevacizumab, VEGF-trap, Retaane® (anecortave acetate); and Combretastatin A4 prodrug. Combination with other forms of ARMD treatment are also feasible, such as one of the preceding treatments in combination with light-activated therapy (for example, photocoagulation, or photodynamic therapy), such as with Visudyne®, vitamins (particular vitamin A, vitamin C, vitamin E, or others), minerals (particularly zinc). Certain embodiments may also be combined with radiation therapy, thermal therapy, surgery, and the like.

The surface charge of the dendrimers can have a significant impact on the intracellular transport and drug release from dendrimers (Kannan, S. et al., *J of Biomaterials Science: Polymers Edition.* 2004; 15(3):311; Khandare, J. et al, *Bioconjugate Chem.* 2005; 60:330-337; Perumal et al., Biomaterials. 2008; 29:3469-3476). The use of such dendrimers to deliver and prolong the local presence of drugs is further supported by the recognition herein that dendrimers were taken up preferentially by microglial cells both in vitro and in vivo, as described in detail in Example 1 herein. PAMAM-generation 4 dendrimers with —OH terminal groups (PAMAM-G4-OH) were effective for microglial cell uptake and intracellular drug release as measured in a rat model.

In vitro, microglial cells were treated with or without FITC-labeled PAMAM-G4 dendrimers having different functional groups, and the uptake was determined using a flow cytometer. Dendrimers with —OH functional groups showed a higher uptake than dendrimers with —NH$_2$ or —COOH functional groups. The —OH dendrimers were rapidly endocytosed by microglial cells.

Amino acid dendrimers have also been suggested. For example, Marano et al. investigated the ability of lipophilic amino acid dendrimers to deliver anti-vascular endothelial growth factor oligonucleotide (ODN-1) into rat eyes to inhibit laser-induced choroidal neovasularization (CNV). (Marano, R. J. et al., *Nature Gene Therapy* 12:1544-1550 (2005)) The nanodevice showed no adverse effects and was tolerated long term. The dendrimer-ODN-1 conjugate was observed to penetrate the retinal cell layers to reach the retinal pigment epithelium. The conjugate showed appreciable efficacy compared to free nucleotide over a four to six month period. The conjugate showed significant efficacy and was present in RPEs at high levels after the first two months. For the delivery of ODN-1, the therapeutic efficacy was comparable to other delivery methods that required an injection every twenty eight days. However, these treatments have disadvantages as demonstrated by their failure to be embraced by the profession and widely used by patients.

The dendrimer-drug conjugates described herein are therefore preferable for treating ocular diseases in which uptake of drug into cells is desired. The drug is chosen on the basis of the disease to be treated, among other factors. The dendrimer size and composition is not limited to those tested herein. Dendrimer sizes suitable for ocular injection include less than about 500 nm, less than about 200 nm, less than about 150 nm, less than about 100 nm, less than about 90 nm, less than about 80 nm, less than about 70 nm, less than about 60 nm, less than about 50 nm, less than about 40 nm, less than about 30 nm, less than about 20 nm, less than about 19 nm, less than about 18 nm, less than about 17 nm, less than about 16 nm, less than about 15 nm, less than about 14 nm, less than about 13 nm, less than about 12 nm, less than about 11 nm, less than about 10 nm, less than about 5 nm, less than about 4 nm, less than about 3 nm, less than about 2 nm, less than about 1 nm, or any value there-between or less.

Dendrimers for ocular use may be composed of polymer micelles that incorporate a pharmaceutical drug. Such polymer micelles may be in the form of a nanoparticle comprising a hydrophilic polymer chain as a shell and a hydrophobic polymer chain as a core. The term "nanoscale" is used herein to denote the full range of sizes below the "microparticle" range, or below one micron (one micrometer) in diameter. It is not limited to a specific size cut-off, and the size ranges provided herein are exemplary. Particle sizes of the micelle include less than about 500 nm, less than about 200 nm, less than about 150 nm, less than about 100 nm, less than about 90 nm, less than about 80 nm, less than about 70 nm, less than about 60 nm, less than about 50 nm, less than about 40 nm, less than about 30 nm, less than about 20 nm, less than about 10 nm, less than about 5 nm, less than about 4 nm, less than about 3 nm, less than about 2 nm, less than about 1 nm, or any value there-between or less.

Some non-limiting examples of hydrophilic polymers that may be used for such an embodiment include a polyalkylene oxide such as polyoxyethylene, polyethylene glycol, polymalic acid, polyaspartic acid and the like. Examples of the hydrophobic polymer which may be used include polylactone, hydrophobic polyamino acid, polystyrene, polymethacrylate ester and the like. A block copolymer may be formed between the hydrophilic polymer chain and the hydrophobic polymer chain. An anionic or cationic charged polymer such as a polypeptide (such as polyaspartic acid), a polyamine or a polycarboxylic acid may be used to form the hydrophobic core. Also, a polyion complex of core-shell type having a core comprising the charged polymer chain and a polymer electrolyte such as a polypeptide, amino acid, or a polypseudo peptide may also be used.

Generally, non-biodegradable or biodegradable polymers may be used to form the microparticles. In the preferred embodiment, the microparticles are formed of a biodegradable polymer. Non-biodegradable polymers may be used for oral administration. In general, synthetic polymers are preferred, although natural polymers may be used and have equivalent or even better properties, especially some of the natural biopolymers which degrade by hydrolysis, such as some of the polyhydroxyalkanoates. Representative synthetic polymers are: poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terephthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly (vinyl acetate), polystyrene, polyurethanes and co-polymers thereof, derivatized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, poly (methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups and other modifications routinely made by those skilled in the art.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the microparticles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

The dendrimer delivery devices are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. A liphatic polyesters differ in hydrophobicity and that in turn affects the degradation rate. Specifically the hydrophobic poly (lactic acid) (PLA), more hydrophilic poly (glycolic acid) PGA and their copolymers, poly (lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

Animal models. Diseases amenable to treatment herein include age-related macular degeneration (ARMD) and retinitis pigmentosa (RP), which share common underlying pathology that can be studied in animals prior to clinical trials. Both diseases exhibit biochemical abnormalities that damage photoreceptors directly and/or indirectly as a consequence of impaired retinal pigment epithelial function. Photoreceptor damage ultimately occurs at the level of cell or mitochondrial membranes. When mitochondrial outer membranes are damaged via lipid peroxidation (usually as a consequence of oxidative stress within the diseased retina), excessive influx of calcium and superoxide anions can occur into the mitochondrial matrix (Marchetti, P., et al. *J Exp Med* 184(3):1155-60 (1996); Green, D. R., et al. *Science* 305 (5684):626-9 (2004); Spierings, D., et al. *Science* 310 (5745):66-7 (2005)). In response to this superoxide and/or calcium overload (calpain-induced apoptosis), the mitochondria release cytochrome c into the cytosol where it interacts with APAF-1 and caspase-9 to form the apoptosome. This apoptotic process leads to the termination of DNA repair, replication, and transduction and cell death. Consequently, antioxidants and drugs that stabilize mitochondrial outer membranes are neuroprotective through their capacity to antagonize apoptotic cell death.

When photoreceptor-surface or other cell-surface membranes within the retina become damaged, microglial cells that are part of the retinal dendritic-cell-mediated immune system, and are normally quiescent under healthy conditions, can become activated to kill and phagocytize the damaged cells. Activated microglia, the mediators of retinal neuroinflammation, release cytotoxic proteins such as tumor necrosis factor-α (TNF-α), reactive oxygen species such as nitric oxide (NO), cytokines, chemokines, proteases and complement. These can all result in photoreceptor cell damage within the outer retina.

The Royal College of Surgeons (RCS) rat retinal neurodegenerative model is suitable for testing treatments for ARMD and RP disease mechanisms as discussed above. The model demonstrates significant apoptotic (Tso, M. et al., *Invest Ophthalmol Vis Sci* 35(6):2693-9 (1994); Katai, N. et al., *Invest Opthalmol Vis Sci* 40(8):1802-7 (1999)) and necrotic cell death as a consequence of activated microglia (Thanos, S., *Brain Res* 588(1):21-8 (1992); Thanos, S. et al., Int J Dev Neurosci 11(5):671-80 (1993); de Kozak, Y. et al., *Ocul Immunol Inflamm* 5(2):85-94 (1997); Akaishi, K. et al. *Jpn J Ophthalmol* 42(5):357-62 (1998); Srinivasan, B. et al., *Science* 310(5745):66-7 (2004); Zeng, H. Y. et al., *Invest Ophthalmol Vis Sci* 46(8):2992-9 (2005)). The neurosensory retina in the RCS rat is biochemically normal. These rats possess an MERTK tyrosine kinase mutation that resides within the RPE. This has been identified to cause RP in humans (Gal, A. et al., *Nat Genet* 26(3):270-1 (2000)).

The MERTK mutation impairs the RPEs capacity to phagocytize shed rod photoreceptor outer segments. The resulting accumulation of aged, peroxidized and damaged cell membranes within the subretinal space (called the outer debris zone) are biochemically similar to drusen in patients with ARMD and act as a potent stimulus for retinal microglial activation. The microglial toll-like receptors bind to the damaged lipid membranes and microglial activation occurs. In the model, healthy photoreceptors die or undergo membrane damage as innocent bystanders when exposed to the cytotoxic proteins, NO, proteases and complement released by the activated microglia. These damaged or dying photoreceptors stimulate additional microglial-cell activation in a neuroinflammatory amplification process that leads to massive photoreceptor degeneration, vision loss and an extinguished electroretinogram (ERG). Phagocytic, rhodopsin-containing activated microglia have been immunohistochemically characterized within the postmortem retinas of patients with RP and ARMD (Gupta, N. et al., *Exp Eye Res* 76(4):463-71 (2003)).

The RCS rat model described above is therefore a suitable animal model for the purposes of the present disclosure, and can be used to test dendrimer formulations and hybrid nanodevices and microdevices comprising dendrimer-drug conjugates and nanoparticles or microparticles encapsulating the conjugates. One of skill in the art will be familiar with use of appropriate controls, although guidance is also provided in the Examples herein.

To test the effect in vivo, healthy rats and rats with active neuroinflammation (retinal degeneration model) were treated with free-FITC and dendrimer-conjugated FITC. In the disease model, the dendrimer-FITC showed enhanced uptake into the outer retina, specially in and among the outer nuclear layer (ONL), activated microglia, and outer debris zone. This pattern of uptake was not observed in the healthy retinas. These data support one advantage of the present dendrimer-drug nanodevices: dendrimer-drug conjugates demonstrate enhanced uptake in retinal sublaminae undergoing active neuroinflammatory and other neurodegenerative processes.

The results from this experiment also showed that dendrimer conjugates were not cleared from the retina as rapidly as free-FITC. This result supports a second advantage of the nanodevices disclosed herein: dendrimer-drug conjugates were capable of prolonging the residence time of drugs in areas of active neuroinflammation such as glia, microglia, retinal pigment epithelium, and blood vessels, enhancing the pharmacodynamic efficacy, targeting specific retinal sublaminae, reducing the overall amount that must be delivered, and potentially reducing drug side-effects.

The FITC was a test molecule to determine dendrimer delivery parameters. Clinical drugs, such as FA and minocycline, are used to test delivery of a biologically active molecule, and minocycline treatment led to suppression of microglial cell activation in vivo. Briefly, postnatal treatment with minocycline decreased the time course of microglial activation as determined by microPET imaging using the microglial specific ligand [$^{11}$C] PK11195. (Example 6.)

Exemplary drugs and therapeutic agents. The choice of drug or pharmaceutical composition will primarily depend on the disease to be treated or condition to be prevented. For example, the synthetic corticosteroid, fluocinolone acetonide (FA) is FDA-approved for chronic intravitreal delivery as part of a sustained-release system for patients with severe uveitis (Jaffe, G. J. et al., *Ophthalmology* 2000; 107:2024-2033; Jaffe, G. J. et al., *Ophthalmology* 2006; 113:1020-1027; Jaffe, G. J. et al., *Investigative Ophthalmology & Visual Science* 2000; 41:3569-3575). Minocycline is known for its anti-inflammatory properties and is used for treating neuroinflammatory conditions.

Minocycline and doxycycline have been shown to reduce inflammation after brain injury. According to the dendrimer-based methods herein, delivering anti-inflammatory agents such as minocycline specifically to microglial cells leads to a decrease in neuroinflammation and hence decreases the injury. Example 6 herein shows that minocycline decreases neuroinflammation by reducing activation of microglia cells.

The Examples were designed to show that the nanodevices can provide enhanced drug delivery, because of their preferential cellular uptake by the microglial cells, and sustained intracellular drug release resulting in significant improvement in therapeutic effectiveness. Experiments were performed in vivo in the rat model of macular degeneration described above. The results are significant and have utility and industrial applicability because dendrimer-based nanodevices can now be developed as a powerful platform in the treatment of neuroinflammation in various ocular pathologies.

An appropriate drug delivery system such as the approach disclosed herein can enhance and sustain the efficacy of these drugs as well as others developed for treating microglia-mediated and other inflammatory diseases of the eye. The results in the Examples herein show that dendrimer-drug conjugates show better therapeutic efficacy in retinal neuroprotection compared to free drug alone or to sustained release drug implants. As one example of this improved route of treatment, the rat model of retinal degeneration was used to compare injected dendrimer-fluocinolone acetonide (D-FA) nanodevices with free FA injections and sustained-release intravitreal drug delivery implants (IDDIs) that release free FA at a sustained daily rate.

FA is currently approved for ocular administration, for example as a sterile implant. The implant is designed to release FA locally to the posterior segment of the eye at a nominal initial rate of 0.6 μg/day, decreasing over the first month to a steady state between 0.3-0.4 μg/day over approximately 30 months. The present compositions improve on the existing treatment, by eliminating the need for implantation and replacing it with a less invasive injection of a dendrimer-FA conjugate.

There was significant preservation of the ERG amplitude with dendrimer-FA treatment when compared to treatment with FA alone or the control untreated rats. Outer nuclear layer cell densities in 9-week RCS rats were compared with data from 0.2 μg/day and 0.5 μg/day IDDIs. Greater cell densities noted in rats treated with D-FA indicates significantly greater neuroprotection in D-FA eyes versus all forms of free-FA ($p<0.001$ for 1 μg and 3 μg D-FA), including IDDIs. Fellow-eye crossover effects were lower in D-FA treated animals as compared to all animals receiving unconjugated FA, including IDDIs.

Without being bound by a mechanism, this seems to be due to the enhanced cell-uptake of D-FITC nanodevices in RCS rats. When D-FA is taken into cells, it is unavailable for re-distribution into the systemic circulation, unlike what is observed with unconjugated drugs. Consequently, the pharmacodynamic effects are enhanced at lower doses. The D-FA injections resulted in greater functional (ERG) and neuroprotective (ONL counts) efficacy at a six-fold lower total FA dose.

Figure 4:
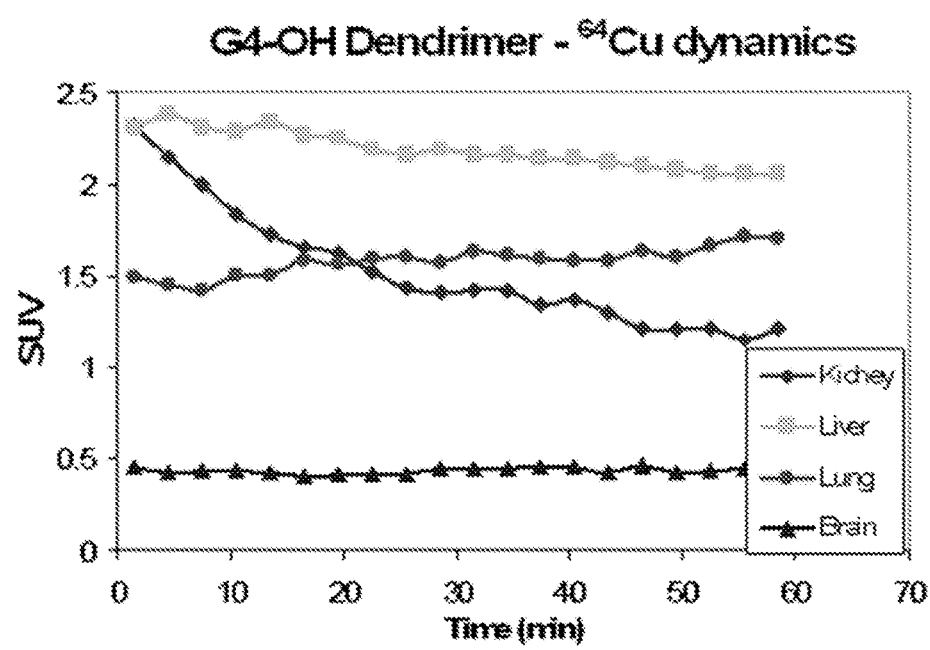
FIG. 4 shows the biodistribution of G4OH—$^{64}$Cu complex in mice. $G4NH_2$ and G4OH dendrimers were complexed with $^{64}$Cu and injected into adult mice to determine biodistribution of the dendrimers with different surface charge. Regions of interest were drawn for various organs, and radioactivity normalized to dose injected and weight of the animal was expressed as standard uptake value (SUV) for each of the organs. Adult mice were injected with 50 uCi of dendrimer-$^{64}$Cu complex IV. The SUV is plotted over time for different organs.

Another important issue in introducing a new treatment is the ability to image uptake and distribution of the targeted drug or device. In the present case of dendrimer nanodevices, dendrimer uptake by microglial cells can be imaged in real time using microPET imaging. To show this, biodistribution of G4OH—$^{64}$Cu complex was examined in mice. (FIG. 4.) G4NH$_2$ and G4OH dendrimers were complexed with $^{64}$Cu and injected into adult mice to determine biodistribution of the dendrimers with different surface charge. Regions of interest were drawn for various organs, and radioactivity normalized to dose injected and weight of the animal was expressed as standard uptake value (SUV) for each of the organs. Adult mice were injected with 50 uCi of dendrimer-$^{64}$Cu complex IV. G4-OH dendrimers showed better brain uptake than the G4-NH$_2$ dendrimers. This shows that imaging in real-time using micro-PET can be used to quantify the uptake of dendrimer-minocycline $^{64}$Cu complexes by microglial cells in the brain.

The dendrimer-conjugate compositions may optionally contain other active ingredients, additives and/or diluents. Injectable compositions may be either in suspension or solution form. In solution form, the complex is dissolved in a physiologically acceptable carrier. Such carriers comprise a suitable solvent, preservatives such as benzyl alcohol, if needed, and buffers. Useful solvents include, for example, water, aqueous alcohols, glycols, and phosphonate or carbonate esters. The dendrimer drug conjugate can be incorporated in vesicles or liposomes.

The conjugate can be encapsulated into a polymeric host system that could either be degradable (i.e., lactic-glycolic acid copolymers or a polyanhydride polymer) or nondegradable (ethylene-vinylacetate copolymer). The conjugate can be incorporated into a hydrogel matrix comprising either poly(hydroxylethylmethacrylate) or poly(vinylalcohol).

Examples 7 and 11 herein provide and disclose microparticles for encapsulating dendrimer-drug conjugates. According to Example 7, PLGA (poly(lactic-co-glycolic acid) microspheres encapsulated dendrimer-FITC conjugates. Methods for manufacturing a PAMAM dendrimer with a protected core are known in the art. The present invention is not limited to any particular dendrimers of specific generations. For example, dendrimers of G1, G2, G3, G4, G5, G6, G7, G8, G9, G10 or greater may be used. Molecular weight and the number of terminal groups increase exponentially as a function of generation (the number of layers) of the polymer. Different types of dendrimers can be synthesized based on the core structure that initiates the polymerization process. In preferred embodiments, the dendrimers comprise G4 dendrimers.

The dendrimer core structures dictate several characteristics of the molecule such as the overall shape, density and surface functionality (Tomalia et al., *Chem. Int. Ed. Engl.* 29:5305 (1990)). Spherical dendrimers can have ammonia as a trivalent initiator core or ethylenediamine (EDA) as a tetravalent initiator core. Recently described rod-shaped dendrimers (Yin et al., *J. Am. Chem. Soc.* 120:2678 (1998)) use polyethyleneimine linear cores of varying lengths; the longer the core, the longer the rod. Dendritic macromolecules are available commercially in kilogram quantities and are produced under current good manufacturing processes (GMP) for biotechnology applications.

Dendrimers may be characterized by a number of techniques including, but not limited to, electrospray-ionization mass spectroscopy, $^{13}$C nuclear magnetic resonance spectroscopy, $^{1}$H nuclear magnetic resonance spectroscopy, high performance liquid chromatography, size exclusion chromatography with multi-angle laser light scattering, ultraviolet spectrophotometer, capillary electrophoresis and gel electrophoresis.

A variety of enteric coating systems can be employed to help the dendrimer drug conjugate pass through the stomach. The dendrimer drug conjugate can be formulated into a tablet using binders known to those skilled in the art. Such dosage forms are described in Remington's Pharmaceutical Sciences, 18th edition, 1990, Mack Publishing Company, Easton, Pa. Suitable tablets include compressed tablets, sugar coated tablets, film-coated tablets, enteric-coated tablets, multiple compressed tablets, controlled-release tablets, and the like.

For treating abnormal or unwanted blood vessel growth, the therapeutic agent can be an anti-angiogenic agent. Examples include anecortave acetate, anti-VEGF aptamer, AMD-FAB, or protein kinase c inhibitor. Other anti-angiogenic agents known in the art may be used. Thus, other anti-angiogenic agents that may be used include, but are not limited to, steroids and angiostatic steroids, metalloproteinase inhibitors, and interferons.

In one non-limiting treatment regimen, PAMAM-G4-OH dendrimers are conjugated with FA and injected into the vitreous of a patient diagnosed with early stage ARMD. The specific concentration and/or formulation of the nanoparticles and/or dendrimers disclosed herein may vary according to any particular disease or condition to be treated. For example, formulations may be administered daily, weekly, monthly, or on an as needed basis, at a drug dose ranging from about at least 1 ng, at least about 1.5 ng, at least 2.0 ng, and so on up to 2000 microgram, at least about 2.0 µm, at least about 2.5 µm, at least about 3.0 µm, at least about 5.0 µm, at least about 8.0 µm, at least about 10 µm, at least about 12 µm, at least about 15 µm, at least about 20 µm, at least about 25 µm, at least about 30 µm, at least about 35 µm, at least about 40 µm, at least about 45 µm, at least about 50 µm, at least about 60 µm, at least about 70 µm, at least about 80 µm, at least about 100 µm, at least about 250 µm, at least about 500 µm, at least about 750 µm, at least about 1000 µm, at least about 1500 µm, at least about 1800 µm, at least about 2000 µm, or any value therebetween.

Efficacy of the treatment can be evaluated according to conventional measurements based on industry standards, including but not limited to evaluation by gross morphology, histology, microbiology, pathology, molecular biology (including analysis of DNA, RNA, or proteins obtained from the treatment subject), as well as input regarding symptoms provided by the subject, if possible.

In one particular embodiment, the dendrimer-FA conjugate is encapsulated in a PLGA nanoparticle and administered to the subject intravenously, orally, buccal, intraperitoneally, into a joint space, rectally, topically, transdermally (particularly for slow release preparations), subcutaneously, intramuscularly, intranasally, intravitreal, suprachoroidal, sub-retinal, episcleral, sub-tenons, intrascleral, epiretinal, injection, by aerosol, or other modes depending on the specific condition or disease to be treated, the organ to be treated, or other factors. Preferably, the nanoparticles comprising the dendrimers disclosed herein are delivered to the eye in the form of eye drops, by deposition of a pellet in or around the eye, by injection into any chamber within the eye, by direct infusion through the eye, and the like. In other embodiments, the inventive nanoparticles comprising the dendrimers disclosed herein are preferably delivered to the nervous system of a subject, preferably the central nervous system. In these particular embodiments, the target cells may include neurons, astrocytes, oligodendrocytes, glial cells or other cells or components associated with the nervous system of the subject.

Alternative nanoparticle formulations include: nanopowders, nanoclusters, nanocrystals, nanospheres, nanorods, nanocups, and other microscopic particles with at least one dimension less than 100 nm.

The Examples below are included for purposes of illustration only, and are not intended to limit the scope of the range of techniques and protocols in which the dendrimer compositions of the present invention may find utility, as will be appreciated by one of skill in the art and can be readily implemented.

EXAMPLES

Example 1

Dendrimer Uptake by Microglial Cells IN VITRO and IN VIVO

The role of surface charge of dendrimers on the intracellular transport and drug release from dendrimers has been reported (Kannan, S. et al., *J. Biomaterials Science: Polymers* Edition. 2004; 15:311; Khandare, J. et al., *Bioconjugate Chem.* 2005; 60:330-337), but not previously reported in relation to microglial cells, a target of the present therapeutic efforts.

To study the effect of dendrimer surface group on microglial cell uptake, microglial cells ($5 \times 10^5$ cells/ml) were treated with or without (Ctrl) 10 µg of FITC-labeled PAMAM-G4 dendrimers with different functional groups (—OH, —NH$_2$ and —COOH) at 37° C. for 1 hour. The uptake of the dendrimers was estimated using a Beckton Dickinson flowcytometer. A significant increase in the fluorescence intensities with the control cells indicated that all three of the dendrimers entered the cells rapidly, with PANAN-G4-OH dendrimers showing a higher uptake than the other two. The results are shown in FIGS. 1A-1D, and indicate that the —OH dendrimers were rapidly endocytosed by microglial cells.

Retinal biodistribution of free-FITC and dendrimer-conjugated FITC (D-FITC) in healthy Sprague-Dawley (SD) and Royal College of Surgeons retinal degeneration model (RCS) rats with active neuroinflammation was studied. Epi-fluorescence histology from retinal cryosections performed 24-hours and ten days after intravitreal injection is shown in FIGS. 2A-2F as follows. (FIG. 2A) D-FITC distribution in normal SD rats at 24-hours; (FIG. 2B) D-FITC distribution in the RCS retinal neurodegeneration model at 24-hours; the concentration of D-FITC within the outer nuclear layer is denoted by *, and a debris zone, where active neuroinflammation is present, is shown; (FIG. 2C) D-FITC is retained within areas of neuroinflammation at ten days; (FIG. 2D) Free-FITC distribution in SD at 24-hours; (FIG. 2E) Free-FITC is uniformly distributed in the RCS rat retina at 24-hours; (FIG. 2F) Free-FITC had cleared from the retina in RCS rats ten days after injection, as shown in FIGS. 2A-2F.

As evidenced by the RCS rat retina in FIG. 2B, the D-FITC demonstrated enhanced uptake into the outer retina, precisely located in and among the ONL, activated microglia and outer debris zone. This pattern of uptake was not observed in any of the healthy SD retinas (FIG. 2A and FIG. 2D). Red in the images is due to autofluorescence from the TRITC filter. The retinal pigment epithelium (RPE) demonstrates enhanced FITC fluorescence in retinas that received D-FITC-containing injections. No FITC fluorescence was observed in the RPE of eyes that received free FITC injections. This pattern was qualitatively similar at ten days post injection. The FITC signal present in FIG. 2F is autofluorescence from the outer-debris zone. The RPE had separated from the retina in this image and was not visible.

These data suggest that cells that have high endocytotic rates, such as activated microglia and retinal pigment epithelium, demonstrate enhanced uptake of D-FITC conjugates. Consequently, the results support the conclusion that dendrimer-drug conjugates demonstrated enhanced uptake in retinal sublaminae undergoing active neuroinflammatory and other neurodegenerative processes. Furthermore, FIG. 2C demonstrates that the dendrimer conjugates were not cleared from the retina as rapidly as free-FITC, FIG. 2F.

This Example shows that dendrimer-drug conjugates are capable of prolonging the residence time of drugs in areas of active neuroinflammation, thereby enhancing the pharmacodynamic efficacy, targeting specific retinal sublaminae, and reducing the overall amount that must be delivered as well as potentially reducing drug side-effects.

Example 2

Figure 6:
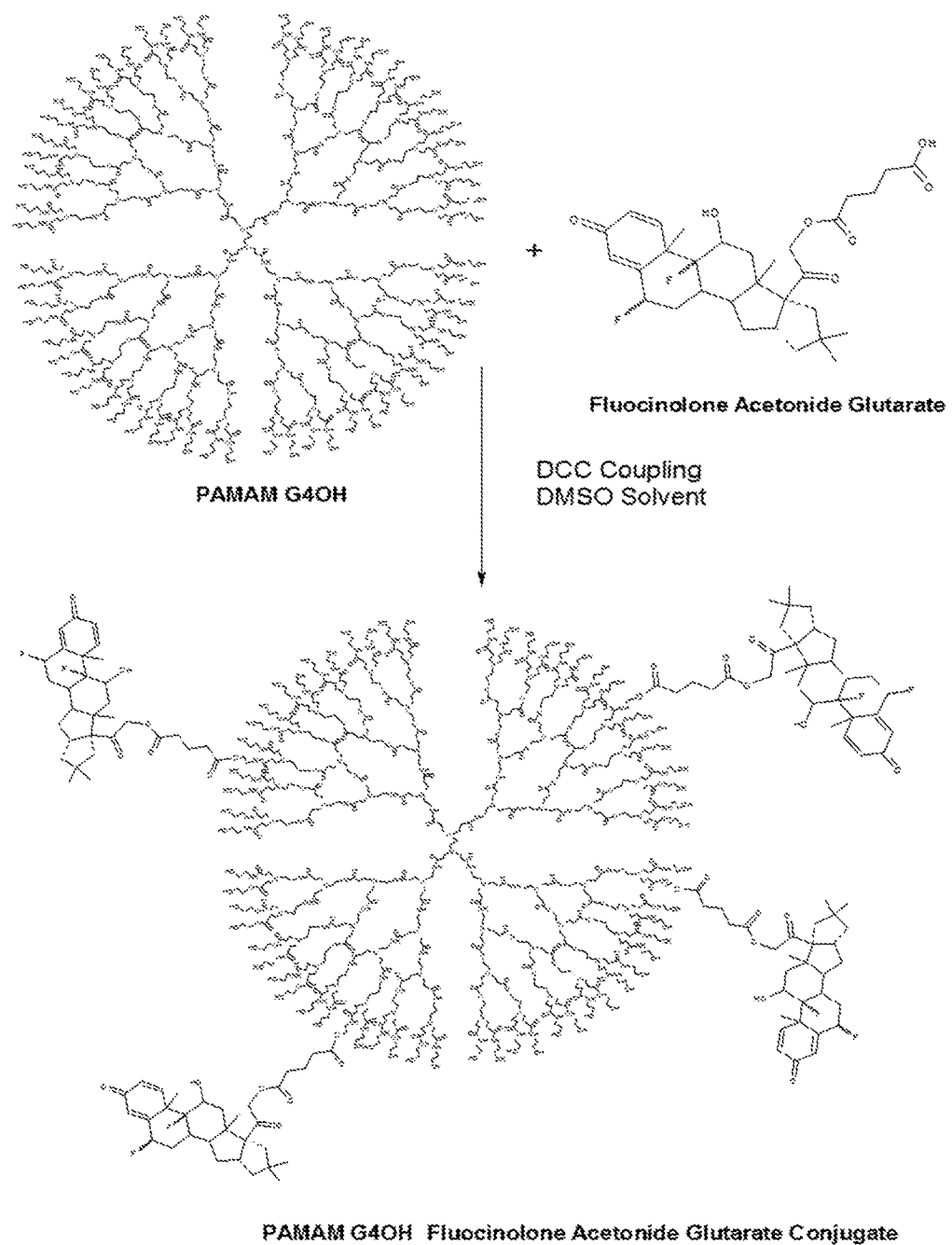
FIG. 6 shows a schematic of the PAMAM-G4-OH dendrimer-fluocinolone acetonide conjugate synthesis. The glutaric acid spacer relieves the steric hindrance on the dendrimer surface, enabling intracellular drug release. The resultant fluocinolone conjugate is water soluble, even though the drug is not water soluble at comparable concentrations

PAMAM-G4-OH-Fluocinolone Acetonide (D-FA) Conjugates (Nanodevices) Compared to Sustained Release Implants Preparation and characterization of D-FA conjugates (nanodevice) were performed as follows. PAMAM-G4-OH dendrimers were chosen for nanodevice preparation. Jayanth Khandare, P. K. et al (2005); P. Kolhe, J. K. et al., *Biomaterials* 27:660-669 (2006). The dendrimers were obtained from Aldrich and were dialyzed to remove any small lower generation impurities that may be present. PAMAM-G4-OH (Mol. Wt=14,217 Da, 64-OH end groups, size~5 nm) was conjugated using a 2-step dicyclohexyl carbodiimide (DCC) coupling reaction (FIG. 6). The reaction mixture was stirred for three days and filtered to remove DCU.

The filtrate was dialysed against DMSO for three days by replacing DMSO after each day (dialysis membrane cutoff 1000 Da) to remove unreacted compounds. The dialyzed product was dried under vacuum to obtain conjugate. $^1$H-NMR was used to characterize the conjugate. The conjugation ratio was 4.5 molecules of FA per molecule of dendrimer and they are soluble in water, as determined by the proton integration method. This suggests a nanodevice molecular weight of 16,700 Da.

These nanodevices were further characterized by MALDI-TOF mass spectrometry, which suggested a molecular weight of 17,000 Da, agreeing well with the NMR data. The stability of the conjugate in DMSO was tested by monitoring the drug release through a dialysis membrane. HPLC analysis of the samples passing to the outside of the membrane collected over a period of 24 hours indicated that a negligible fraction of drug from the conjugate was released. This suggests that the conjugate is very stable, and that free (i.e., unconjugated) FA in the conjugate was minimal after purification.

Neuroprotective effects of dendrimer-FA (D-FA) nanodevices were determined as follows. The neuroprotective effects of intravitreally-injected D-FA nanodevices to free-FA injections and IDDIs that release free-FA at a sustained daily rate were compared. FIG. 3A shows mean ERG b-wave amplitudes in 9-week RCS rats, four-weeks after a single 1 µl right-eye injection of 1 µg or 3 µg dendrimer-FA (D-FA) or unconjugated, free-FA. There is significant preservation of the ERG amplitude with dendrimer-FA treatment when compared to treatment with FA alone or the control untreated rats. FIG. 3B shows ONL cell densities for 1 µg and 3 µg injections of D-FA and free-FA, in addition to the same data for IDDIs shown in FIG. 9B. Here the 1 µg and 3 µg refer to the FA content in D-FA. ONL cell densities were higher for D-FA than those measured for IDDIs and free FA injections. ONL dell densities were significantly higher in 1 µg and 3 µg D-FA injection groups that in free-FA 1 µg ($p<0.001$ for 1 µg and 3 µg D-FA). The fellow-eye crossover effects, described in Example 6 for IDDIs and that seen with free-FA 1 µg and 3 µg injections in FIG. 3B, were less pronounced for the D-FA injected eyes.

FIG. 7 shows microglia counts within the outer debris zone in the retine of nine week-old control rats and rats given different doses of fluocinolone acetonide.

Without being bound by a specific mechanism, this is likely due to the enhanced cell-uptake of D-FITC nanodevices in RCS rats as demonstrated in FIGS. 5A-5D. When D-FA is taken into cells, it is unavailable for re-distribution into the systemic circulation as is observed with unconjugated drugs. Consequently, the pharmacodynamic effects are enhanced at lower doses. The D-FA injections resulted in greater functional (ERG) and neuroprotective (ONL counts) efficacy at a six-fold lower total FA dose.

Example 3

Fluocinolone Acetonide was Neuroprotective in RCS Rats

Figure 9A:
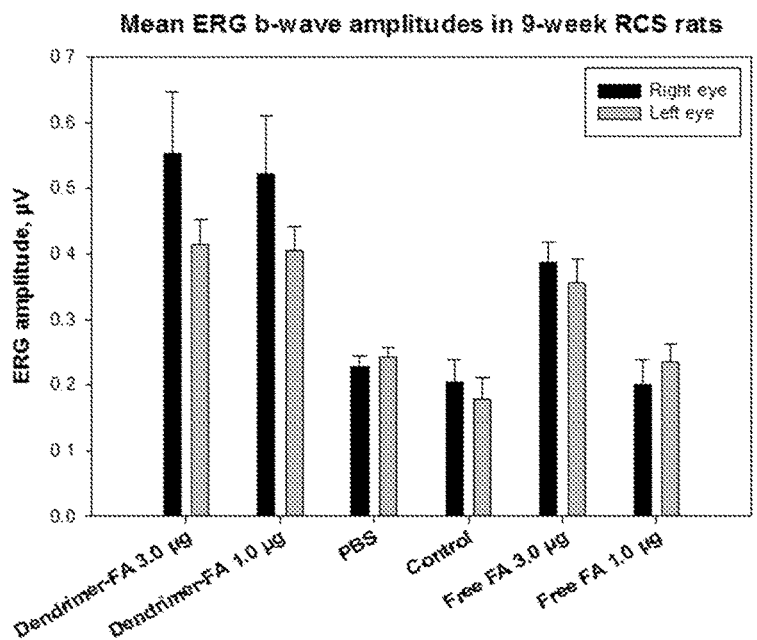
FIGS. 9A and 9B are bar graphs showing (FIG. 9A) the mean ERG b-wave amplitudes in RCS rats treated with 0.2 µg/day and 0.5 µg/day sustained doses of FA over four-weeks in the right eye, compared to non-surgical and inactive drug-delivery implant groups, and (FIG. 9B) Mean outer nuclear cell density across the same four groups of RCS rats, according to retinal quadrant.
Figure 9B:
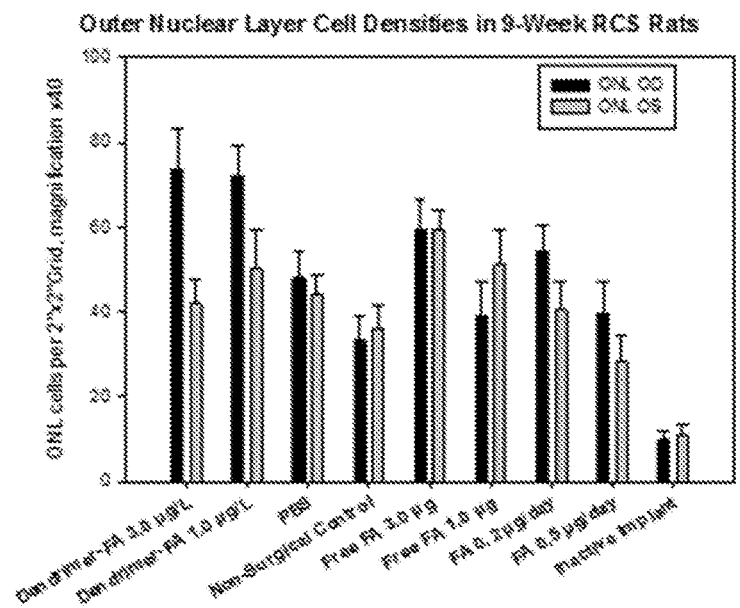

According to this Example, the steroid fluocinolone acetonide (FA) was highly neuroprotective in slowing the retinal degeneration of RCS rats when delivered via sustained-release intravitreal drug delivery implants (IDDIs). FIG. 9B shows outer nuclear layer cell (photoreceptor cell body) densities among four-groups of nine-week RCS rats that received either FA 0.2 µg/day, FA 0.5 µg/day, inactive drug-delivery implants (in right eyes) and non-surgical controls during the four-week study period. Quantitative histological analysis showed that the ONL cell densities in FA 0.2 µg/day-treated eyes were 2.38±0.12 times greater than in the non-surgical controls ($p<0.001$) and 4.85±0.24 times higher than in the inactive IDDI group ($p<0.001$). In the FA 0.5 µg/day-treated eyes, ONL counts were 1.78±0.21 times greater than the non-surgical control eyes (p-value with Kruskal-Wallis test=0.02) and 3.56±0.17 times higher than eyes that received inactive IDDIs ($p<0.001$). No significant differences were observed in the inner nuclear layer cell counts between groups.

In other experiments, fluocinolone acetonide preserved electroretinogram b-wave amplitudes in treated eyes. The ONL data were consistent with ERG findings in the same animals (FIG. 9A). Comparison across groups showed that mean four-week postoperative ERG b-wave amplitudes recorded from 0.2 µg/day and 0.5 µg/day FA-treated eyes were significantly greater than those of the unoperated control and placebo-treated eyes ($p<0.001$). ERGs supported the observation made in ONL cell count data that the lower daily dose group demonstrated greater neuroprotective and functional efficacy. Although mean b-wave amplitude values in the eyes treated with FA 0.5 µg/day were quantitatively lower than the values in the eyes treated with FA 0.2 µg/day, there was no statistically significant difference between them (p=0.113).

IDDIs demonstrated a dose-related cross-over effect in RCS rats. Quantitatively, the left eye-ERG b-wave amplitudes of the FA 0.2 µg/day-treated group at the four-week time point were greater than those of control right and left eyes and placebo group-right and left eyes. Mean ERG b-wave amplitudes of left eyes of FA 0.5 µg/day-group were significantly different from those of right and left eyes of unoperated control animals ($p<0.03$, with power of analysis 0.050:0.810, Kruskal-Wallis p=0.006). No statistically significant differences in mean ERG b-wave amplitudes of left eyes of FA 0.2 µg/day-treated group versus right or left eyes of placebo-treated group or right or left eyes of control animals was found. The fellow-eye effects were attributed to drug-crossover. This is commonly seen in small mammals in which the volume of distribution is small. The observation of a dose-related fellow-eye treatment response indicates that free-drug is likely leaving the eye via the episcleral and/or vortex venous systems and becoming systemically distributed, after which it exhibits pharmacodynamic effects in the fellow-eye.

FA suppressed neuroinflammation in RCS rats. In examining the mechanism of action of FA in preserving the ONL and ERG in the RCS rat, quantitative histological analysis of activated retinal microglial cells were performed using ED-1 immunolabelling. The photoreceptor layer and outer debris zone in RCS rats contain damaged lipid membranes that amplified photoreceptor damage by activating microglia to become phagocytic and release toxic substances such as tumor-necrosis factor alpha (TNF-α). Activated microglial cell densities in the debris layer of FA 0.2 µg/day-treated eyes showed a five-fold decrease compared to the non-surgical control eyes ($p<0.001$) and nine-fold decrease compared to eyes that received inactive IDDIs ($p<0.001$). In the FA 0.5 µg/day-treated eyes, the debris zone activated microglial density was four times lower than non-surgical control eyes ($p<0.001$) and seven times lower than in eyes that received inactive IDDIs ($p<0.001$).

Example 4

Figure 5:
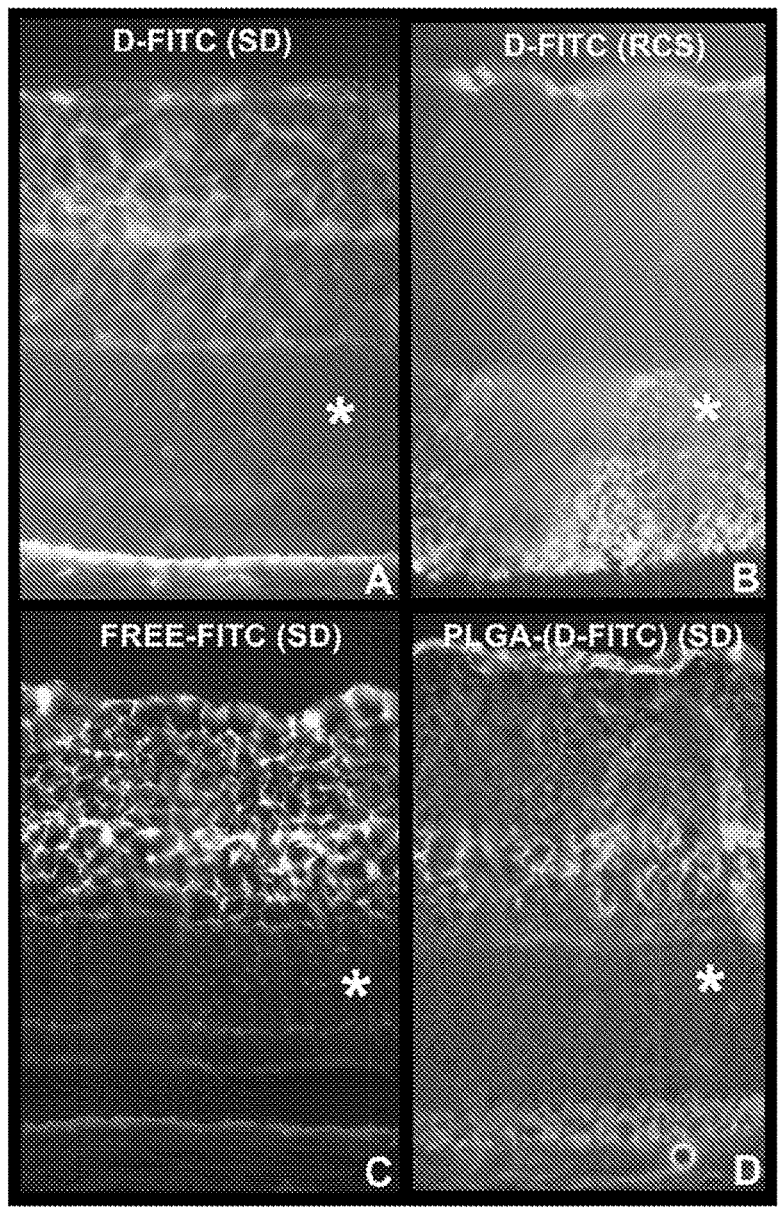
FIGS. 5A-5D show a 24-hour post-injection histology of FITC.

PAMAM-G4-OH Dendrimers Show Enhanced Uptake in the Outer Nuclear Layer of Degenerating RCS Rats, But Not in Normal SD Rats FIGS. 5A-5D show epifluorescence histology from retinal cryosections in Sprague-Dawley (SD) and RCS rats. These were made twenty four hours after intravitreal injection with free, unconjugated FITC, dendrimer-conjugated FITC (D-FITC), and D-FITC encapsulated in PLGA microspheres (PLGA-(D-FITC). In examining the RCS rat retina in FIG. 5B, it is apparent that the D-FITC demonstrated enhanced uptake into the outer retina, precisely located in and among the ONL, activated microglia and outer debris zone. This pattern of uptake was not observed in any of the healthy SD retinas (FIG. 5A, FIG. 5C, and FIG. 5D). Red in the images is due to autofluorescence from the TRITC filter.

The retinal pigment epithelium (RPE) demonstrates enhanced FITC fluorescence in retinas that received D-FITC-containing injections. No FITC fluorescence was observed in the RPE of eyes that received free FITC injections. This pattern was qualitatively similar at 10-days post injection. These data suggest that cells that have high endocytotic rates such as activated microglia and retinal pigment epithelium demonstrate enhanced uptake of D-FITC conjugates. Consequently, Dendrimer-FA (D-FA) conjugates likely demonstrate enhanced uptake in retinal sublaminae undergoing active neuroinflammatory and other neurodegenerative processes.

Example 5

PLGA Microparticles Prepared with Encapsulated Dendrimer-FITC Conjugates

PLGA microparticles were prepared with encapsulated dendrimer-FITC conjugates as follows. The water-in-oil-in-water (w/o/w) method is suited to encapsulate water-soluble nanodevices like dendrimer-drug conjugates, unlike the o/w method which is ideal for water-insoluble drugs like such as FA. (Jayanth Panyam, M. M. D. et al., *Journal of Controlled Release* 92:173-187 (2003); Jayanth Panyam, S. K. S. et al., *International Journal of Pharmaceutics* 262:1-11 (2003)). Appropriate amounts of PLGA (Mol. Wt. 90,000-125,000 Da,; 75% PLA/25% PGA) were dissolved in chloroform. Separately, a 2.5% solution of PVA was prepared in cold distilled water, saturated with chloroform.

An aqueous solution of dendrimer-drug conjugates (10% W/V) was added, in two portions, to the PLGA solution with vortexing for one minute after each addition. It was then placed on an ice bath for five minutes and then emulsified using FS 20 Bath sonicator (44-48 KHz, Fisher scientific) for one minute to obtain water-in-oil emulsion. The primary emulsion was then added in two portions to 8 ml of the PVA solution with intermittent vortexing to obtain the multiple w/o/w emulsion.

The emulsion was placed on an ice bath for five minutes and then sonicated for three minutes. The emulsion was stirred overnight on a magnetic stir plate to allow the evaporation of chloroform and the formation of the nanoparticles. The suspension was transferred into ultra-clear centrifuge tubes and centrifuged at 14,000 rpm for thirty minutes at 4° C. in an ultracentrifuge. The pellet was resuspended in distilled water and sonicated for thirty seconds on an ice bath to disperse any aggregates. Centrifugation was repeated two more times at 14,000 rpm, thirty minutes to remove PVA and unencapsulated conjugates from the formulation. The scanning electron microscopy (SEM) and particle size analyzer were used to assess particles sizes. Even though the mean particle size was ~5-10 μm, there was some polydispersity. Fluorescence microscopy suggested that the D-FITC conjugate was "uniformly" encapsulated.

Drug release from PLGA microspheres was studied as follows. The drug release kinetics for free fluocinolone acetonide was analyzed for the same PLGA microspheres. For ~5 -10 μm microspheres (containing 5% by mass of FA), the release was ~0.5 μg/day (average) for the first thirty days, with a cumulative release of ~30% in one month. There was 3% initial burst in the first three days. For dendrimer-FA conjugates, the initial burst may be capable of elimination due to their relatively larger size.

Example 6

Minocycline Treatment Led to Suppression of Microglial Cell Activation IN VIVO According to this Example, postnatal treatment with minocycline decreased the time course of microglial activation as determined by microPET imaging using the microglial specific ligand [$^{11}$C] PK11195. To demonstrate microglial inhibition with minocycline treatment, [$^{11}$C] PK11195 uptake in pups at postnatal day 5 with and without minocycline treatment was determined by PET imaging.

As shown in FIGS. 8A-8F, a decrease in the [$^{11}$C] PK11195 uptake from the first ten minutes to the last ten minutes (similar to control pups) was seen in the postnatal day five pup exposed to endotoxin in utero that was treated with minocycline 15 mg/kg for three days suggestive of a decrease in activated microglial cells. An increase in the PK11195 uptake is noted in the untreated endotoxin exposed pup in the last ten minutes when compared to the first ten minutes, suggestive of continued presence of activated microglial cells in the untreated endotoxin pups. This indicates that minocycline treatment resulted in inhibition of activated microglial cells in the endotoxin exposed pup.

Postnatal treatment with minocycline improved neurobehavioral outcome at postnatal day eight, as evidenced by neurobehavioral testing of rabbit pups at postnatal day eight. The following animals were observed: (A) control pup, (B) pup exposed to endotoxin 20 μg/kg in utero treated with PBS; and (C) endotoxin 20 μg/kg pup treated with 15 mg/kg of minocycline, at day eight of life. The endotoxin-exposed pups were more wobbly, with increased tone and decreased balance when compared to the control pups. Hindlimbs were abducted with full range of motion in the control pup A and in the pup treated with 15 mg/kg of minocycline (C) but not in the untreated pup (B). Hindlimb tone was greater in pup (B) leading to uncoordinated locomotion and decreased balance.

A dose response for free minocycline in this model showed that 15 mg/kg of minocycline demonstrated greater improvement in motor deficits when compared to 5 mg/kg. A decrease in the white matter injury, which would result in the improvement in motor deficits due to suppression of microglial activation was confirmed by diffusion tensor imaging (DTI) and immunohistochemistry. In conclusion from this Example, minocycline has a specific and clinically relevant effect by reducing the endotoxin-associated activation of microglial cells in rabbit pups in utero. This drug and others with similar effects are suitable for targeting microglial cells using dendrimer compositions disclosed herein.

Example 7

Rat Model for Macular Degeneration

Dose-ranging of minocycline is studied for photoreceptor neuroprotection and suppression of retinal neuroinflammation. The goal of this Example is to determine the efficacy of dendrimer-minocycline nanodevices (D-Mino). Based on the efficacy observed when conjugating fluocinolone acetonide to dendrimers, this Example is designed to evaluate the efficacy of D-Mino conjugates in suppressing retinal neuroinflammation associated with the RCS rat neurodegeneration model. Minocycline is used because it highly neuroprotective and suppresses microglia in the RCS rat retina. Chang, C. J. et al., *Ophthalmic Res.* 2005; 37:202-13; Hughes, E. H. et al., *Exp Eye Res.* 2004; 78(6): 1077-84; Shimazawa, M. et al., *Brain Res.* 2005; 1053:185-94; Zhang, C. et al,. *Invest Ophthalmol Vis Sci.* 2004; 45:2753-9.

A dose-ranging study is conducted to identify the most efficacious dose of intravitreally-injected unconjugated minocycline (Free-Mino) for retinal neuroprotection in the RCS rat. D-Mino doses are determined based upon the optimal Free-Mino doses and upon FA data. The same five-week homozygous recessive rdy albino RCS rat model used in Example 8 is used.

Four groups of five animals are established. These include intravitreal injection groups receiving 1 µg Free-Mino, 10 µg Free-Mino, a phosphate-buffered-saline (PBS)-(free-dendrimer), and a PBS injection control group. The PBS-(free-dendrimer) group is used to rule out any neuroprotective effects from dendrimers alone. Animals undergo bilateral intravitreal injections, according to established methods. Animals are euthanized at one-month for quantitative histological analysis of photoreceptor and microglial cell counts within retinal sublaminae. Briefly, photoreceptors are counted from 6-µm H&E retinal sections. Retinal microglia are counted from IBA-1 and ED-1 labelled retinal slices and wholemounts.

The b-wave ERG amplitudes in RCS rats are recorded as a measure of photoreceptor function, once every two weeks, according to well-established methods. A second four-week dose-ranging study is conducted with Free-Mino, based upon the results of the first study to improve the optimal-dose measurement.

Subsequently, a four-group dose-ranging study for D-Mino is performed, using the same methods. Initial doses are based upon the relative potency of D-Mino to Free-Mino, according to the data for FA of Example 2. The D-Mino dose is further refined in a second study, based upon the degree of neuroprotection and upon the degree of microglial suppression observed in the minocycline studies, compared to the FA and Free-Mino results, The FITC biodistribution data in FIGS. 2A-2F demonstrate the improved localization (FIG. 2B) and residence time (FIG. 2F) that dendrimer conjugation confers to drugs. The optimal dosing interval for D-Mino is measured by performing a three-month study, similar to those outlined in this Example, however re-dosing D-Mino, based upon a 10% decline in ERG amplitude (measured once every two-weeks). In this way, a measure of retinal function is used to establish the first two-week time point when the prior D-Mino injection shows loss of efficacy. By re-dosing, based on retinal function, ERG stabilization should be restored. Over the course of the three-month study, the dose-interval that prevents progressive ERG amplitude loss will also be the optimal one. In addition, this will determine the duration of action for a single D-Mino injection.

Example 8

Biodistribution and Residence Time of Free-FITC and D-FITC

The goal of this Example is to identify dendrimer-fluocinolone (D-FA) dosage requirements for sustained retinal neuroprotection using intravitreal injections of free-FITC and D-FITC. The experiments are performed in homozygous recessive rdy albino RCS rats of both genders, aged five-weeks, weighing 150-180 grams. Two-groups of animals are established. The free-FITC group consists of six animals that each receive bilateral injections of free-FITC, 1 µg. Another group of ten animals receives intravitreal injections of D-FITC.

Prior to injection, the animals are anesthetized with ketamine (100 mg/kg) and xylazine (10 mg/kg) via IP injection. A 1 µL volume of 1 µg FITC dissolved in a small amount of DMSO is injected via a Hamilton syringe into the vitreous cavity of each eye. Animals injected with free-FITC are euthanized at 10-days, one-month and two-months. The eyes are enucleated, bisected, and the half globes are embedded in Tissue-Tek OCT Medium (Sakura Finetek, U.S.A., Torrance, Calif.) and then quick frozen in liquid nitrogen. Sections (14 µ) are cut on a cryostat (Leica Instruments, GmbH, Nussloch, Germany), mounted (still frozen) on slides with Vectashield (Vector Laboratories, Burlingame, Calif.) and examined by epifluorescence digital imaging using separate FITC and TRITC filter cubes.

Pictures are taken using a MagnaFire digital camera (Olympus America, Melville, N.Y.). The images are evaluated for retinal sublaminae that are labelled for each time-point. In addition, the relative amount of fluorescence intensity is compared between slices, imaged at each time-point after the illuminator and the camera settings have been adjusted to pre-determined brightness and exposure settings. The epifluorescence illumination setting is adjusted according to the CCD image intensity value measured at pre-determined camera aperature and exposure settings, using a standardized low-concentration of FITC. This FITC-signal calibration process allows comparison of the relative intensity of FITC within each retinal sublamina as a relative measure of the tissue persistence of FITC. The same procedure is performed in animals that receive a 1 µL volume of 1 µg D-FITC. In this way, the relative differences in free-FITC and D-FITC biodistribution and tissue persistence are compared, since the CCD camera has a highly linear output.

The D-FITC group consists of ten animals that are euthanized and enucleated for cryosection epifluorescence imaging at 10-days, one-month, two-months, four-months and six-months. For both experimental groups, the fellow eye from each animal that has also undergone intravitreal injection of free-FITC or D-FITC is utilized for fluorophotometric assay of vitreous fluorescence and for FITC fluorescence of tissue homogenates. This allows determination of the relative amount of free-FITC or D-FITC within the vitreous and the tissue of each eye at each time-point. A third group of animals is included, concurrently to examine the biodistribution and tissue persistence of PLGA-(D-FITC). A fourth control group, consisting of one-animal per time-point, serves as bilateral vehicle-injected controls to establish baseline levels of tissue autofluorescence.

Estimation of D-FITC in the eye is performed as follows. For the biodistribution study, at monthly intervals, the eyeball is collected and the tissue is homogenized and dissolved in NaOH. Using a combination of solvent extraction with methanol (D-FITC is soluble in methanol), and further re-suspension in PBS, the D-FITC is extracted. The D-FITC content is quantitated, using a UV/Vis and fluorescence calibration curve previously prepared at various D-FITC concentrations.

Assessment of the duration of pharmacodynamic effect of single 0.2 µg and 1 µg D-FA injections, as well as the dose-interval require to maintain the retinal function of RCS rats, in vivo, is performed as follows. One goal is to isolate the efficacy of D-FA nanodevices, as specifically as possible, with appropriate controls. This experiment is performed to examine the duration of action of single intravitreal injections of 0.2 µg and 1 µg D-FA in homozygous recessive rdy albino RCS rats of both genders, aged five-weeks, weighing 150-180 grams. Here, 0.2 µg and 1 µg refer to the FA content in the D-FA injections.

Four groups of ten animals are established. These include an intravitreal injection group receiving 1 µg D-FA, a group receiving 0.2 µg D-FA, a group receiving PBS solution containing (2% DMSO with 1 µg free-FA and free-dendrimer) in equivalent amounts to the 1 µg D-FA group, and a non-surgical control group. The PBS-(free-FA, free-dendrimer) group is used to isolate the efficacy of dendrimer-conjugated FA (D-FA). Animals undergo bilateral intravitreal injections, according to the methods described above. Five animals from each group are euthanized at one-month and at three-months for quantitative histological analysis of photoreceptor cell counts and microglial cell counts within retinal sublaminae. These are performed using the methods described below.

The b-wave ERG amplitudes are recorded in RCS rats as a measure of photoreceptor function, once every two-weeks, according to the methods below. The time interval from the current injection to the prior injection is used as one datum in determining the appropriate dosing interval and duration of action for the two D-FA doses, 0.2 µg and 1 µg when administered as single bolus intravitreal injections. In addition, the control injection group is re-injected at the same time points that the D-FA 1 µg group is. This will assure that the control group receives that same number of injections that the D-FA 1 µg group.

Electroretinography is performed as follows, using stimulation, recording and data analysis routines developed using Labview software (National Instruments, Austin Tex.). Animals are dark-adapted for 12-hours overnight. Prior to testing, animals are anesthetized with an intraperitoneal injection of Ketamine 67 mg/kg and Xylazine 10 mg/kg. Pharmacological mydriasis is induced, bilaterally with 1% Tropicamide and 2.5% Phenylephrine. Topical 0.9% saline is periodically applied to the corneas to prevent dehydration. ERG responses are recorded using platinum wire loop corneal electrodes, from both eyes simultaneously. Reference platinum needle electrodes are placed in the ears. White clear LEDs CMD204 (UWC Series T-1), with a luminous intensity of 1000 mcd, are employed for flash stimulation. Fifteen 1-millisecond flashes are delivered to both eyes simultaneously with constant 10-second inter-stimulus intervals. The ERG responses are amplified using a gain of 5000, bandpassed between 10 and 100 Hz.

ERGs are averaged and mean b-wave amplitude is determined for each animal at each time point. If the ERG b-wave amplitude has declined by 10% from the average of previous two recording sessions, then a re-dose intravitreal injection is performed according to the methods outlined above.

For histology, the eyes are enucleated and placed in Karnovski's fix overnight, at 4° C. After an 18 hour immersion period, eyes are rinsed with 0.01 M phosphate buffer solution. Eyes are prepared for sectioning, by making a transverse cut along the horizontal meridian. After grossing, eyes are dehydrated in serial dilutions of alcohol, cleared with Pro-Par (Xylene-substitute, Anatech Ltd., Battle Creek, Mich.) and embedded in paraffin containing DMSO (Fisher). Serial 6 µm-thick whole-eye sections are obtained. Paraffin sections are mounted on Poly-L-lysine coated glass slides and stained using Harris' Haematoxylin and Eosin.

Microglia staining in whole-mounted retina is performed as follows. Rat eyes are enucleated and fixed briefly in buffered ten percent formalin. They are then bisected and the nasal section fixed for a further 4 hours at 4° C. The temporal section is embedded in OCT compound (Sakura Finetek, USA Inc., Torrance, Calif.) and flash-frozen in liquid nitrogen for cryo-sectioning. Orientation is preserved for each section.

After fixation, as detailed above, the retinas are carefully removed and placed in PBS containing 1% Triton X-100 for one hour at room temperature. Retinas are then incubated overnight at 4° C. in a cocktail of Iba-1 antibody (Wako Chemicals USA Inc, Richmond, Va.) at 1:200 dilution and ED-1 antibody (Serotec Ltd. Oxford, UK) at 1:100 dilution, in PBS containing 0.1% Triton X-100 and four percent normal goat serum. After several washes, retinas are incubated in the appropriate fluorescently labeled secondary antibody (Sigma-Aldrich, St. Louis, Mo.) solution for two hours at room temperature, mounted ILM side down on glass slides and cover-slipped with Vectashield (Vector Laboratories, Burlingame, Calif.).

Microglia staining in transverse retinal sections is performed as follows. Sections (10-micron) are cut on a cryostat (Leica Instruments GmbH, Nussloch, Germany), recovered on Vectabond (Vector Laboratories, Burlingame, Calif.) coated slides and fixed for one minute in acetone. Slides are allowed to air dry and are stored at 4° C. until used. Sections are then re-hydrated in Tris buffered saline (pH 7.4) and non-specific staining blocked with 5% normal goat serum. Sections are incubated in Iba-1 and ED-1 antibody solution, as detailed above, and developed for fluorescence microscopy using the appropriate fluorescently labeled secondary antibodies.

For each eye, ERG waveforms are averaged over fifteen traces for each recording session. The b-wave amplitude is defined as the peak-to-peak amplitude of the leading positive slope (from the lowest point of the a-wave to the highest point of the b-wave). This is measured from each of the averaged ERG waveforms. Mean and standard deviation b-wave amplitude are measured for each eye of each animal for each time point. Group means and standard deviations are also computed for right and left eyes at each time point. Parametric and non-parametric statistical analyses are performed on these data.

For histological cell count analysis, retinal photomicrographs are taken of both right and left eyes, using an Olympus B-MAX 50 microscope (Japan), with Olympus Magnafire PM30/PM20 digital camera, at 40× magnification. In all eyes, five photomicrographs are taken in each of the four retinal quadrants (i.e., twenty photomicrographs per eye): 1) superior temporal; 2) superior nasal; 3) inferior temporal; 4) inferior nasal. Care is taken to precisely correlate these regions between eyes.

Each photomicrograph is analyzed using a grid counting method. A masked observer counts the number of outer nuclear layer (ONL) and inner nuclear layer (INL) cells in each of the two grid regions defined per photomicrograph. The counts are averaged for the ONL and INL in each tested retinal region for right and left eyes in each group.

For microglial cell count analysis, positively stained microglial cells are counted using an Olympus B-MAX 50 microscope (Japan) with the appropriate filter sets. In retinal whole-mount preparations, counts are made in six standardized fields at three defined levels within the retina: a layer at the level of inner limiting membrane (ILM layer), a layer at the level of inner plexiform layer (MID layer), and a layer at the level of retinal photoreceptors (PHR layer). In retinal transverse sections, activated microglia are counted in the photoreceptor debris zone in two superior and two inferior retinal fields.

One way ANOVA with concomitant paired t-test, when valid, is performed for both the 4-week postoperative ERG data and the averaged ONL and INL cell count data across treated and untreated eyes in all groups. The measured microglial cell count values are averaged to calculate means and standard deviations for every microglial cell layer among experimental groups. The analyzed data are graphed. Although power of analysis established that five animals per group are adequate to perform parametric statistical comparisons, a non-parametrical (Kruskal-Wallis or Mann-Whitney) analysis can be performed every time a one way ANOVA is applied.

Example 9

Assessment of Sustained Intravitreal D-FA Efficacy IN VIVO

The present Example is designed to study sustained D-FA delivery via repeated intravitreal injections, at the appropriate dose and at the appropriate dosing interval for sustained retinal photoreceptor neuroprotection and preservation of the ERG b-wave amplitudes in RCS rats. Using either 0.2 µg or 1 µg D-FA injections (on a drug basis), RCS rats are divided into two groups of fifteen animals. Animals from one group undergo intravitreal injection of D-FA while the other group receives PBS containing (2% DMSO with free-FA and free-dendrimer). ERG recordings are performed once per month. D-FA and control re-injection are performed when ERG b-wave amplitudes in the D-FA group have declined by 10% as compared to the mean of the two-previous ERG recordings.

Five animals per group are euthanized at months three, seven, and nine for quantitative histological analysis of photoreceptor cell counts, total microglia and microglial localization, as well as number of activated microglia. By summing the total D-FA required to maintain ERG amplitudes, and dividing this number by the duration of neuroprotection, the required release rate of D-FA to maintain ERG amplitudes from sustained-release PLGA-(D-FA) is estimated.

From this Example, the dosage and the interval to maintain the function of the retina can be determined, since only a 10% reduction in the ERG is allowed. The control allows the effect of the nanodevice to be determined. The residence times of the dendrimers in the vitreous can be determined, as well as the cellular distribution in the retinal sublaminae. If the dendrimers are found in the outer retina beyond at least two to three weeks, the efficacy of the nanodevices could last for significantly longer than one month and provide long-term treatment. Therefore, this Example provides additional data for evaluating long-term clinical effectiveness of the devices disclosed herein.

Example 10

Injectable, Sustained-Release Intravitreal Drug-Delivery Platform Based Upon Hybrid [PLGA-(D-FA) Nanodevice] Microspheres This Example is performed to determine the biodistribution and residence time of PLGA-(D-FITC) microspheres. A group of ten animals is added to the biodistribution study of Example 9, and these animals undergo bilateral intravitreal injection of PLGA-(D-FITC) microparticles. These animals are euthanized at 10-days, one-month, two-months, four-months and six-months.

PLGA-D-FA microspheres are prepared with the intent of achieving sustained delivery of ~0.03 µg/day of FA in D-FA for 180 days. One intravitreal injection of 1.0 µg D-FA is effective for one-month (0.03 µg/day). Thus, the dendrimer-FA conjugate is estimated to clear the vitreous chamber in a few days. A significant portion of these appear to be taken in by the ONL, where the drug is released over a period of time, in a manner that suggests that the pharmacodynamic effect lasts for about a month. Therefore, an appropriately designed PLGA microsphere encapsulation of the D-FA will provide a controlled release of D-FA, which will then enter the retinal cells and release the drug.

The size and molecular weight of the D-FA conjugates (~7 nm, ~20 kDa) are comparable to small proteins. In PBS (pH=7.4), the ester bond between the drug and dendrimer is stable. The hydrolysis of this bond most likely occurs over a period of time in the acidic lysosomal pH. Therefore, appreciable drug release from the dendrimer inside the PLGA microsphere is not anticipated, especially with 75% PLA. (DD 1990; P. Kolhe 2006).

It has been previously shown that PLA microspheres can last as long as long as sixty days in PBS buffer of 7.4 pH. PLGA microspheres of size ~10 µm and of copolymer composition 90% PLA and 10% PGA (PLGA(90:10)) also resist degradation for extended periods. (DD 1990). This size of the microsphere also significantly improves the intravitreal residence time. PLGA (75:25) is used for sustained delivery of the drug to the eye. Based on diffusion coefficients of larger molecules (~$10^{-13}$ cm$^2$/sec) from PLGA microspheres, the D-FA diffusion is expected to take place over a period of months, thereby providing sustained drug delivery over a six month period. (Sandora 2001)

The PLGA microparticles (composition: 75% PLA/25% PGA, molecular weight ~90-125 kDa) containing dendrimer-FITC (for biodistribution studies) and dendrimer-FA (for release studies and in vivo efficacy studies), are prepared using a water-in-oil-in water (w/o/w) method as described in the Examples. (Sanjeeb K Sahoo, J. P. et al., *Journal of Controlled Release* 82:105-114 (2002); Jayanth Panyam 2003). The solution of particles is filtered to produce a particle size in the range of ~5-10 µm. The particle size is characterized by SEM and a Malvern particle sizer. The presence and distribution of nanodevice inside the microparticle is assessed with an encapsulated D-FITC nanodevice, using fluorescence and confocal microscopy.

For in vitro release studies, PLGA-dendrimer-FA microspheres are placed in a micro centrifuge tube containing 250 µl of 0.1 M phosphate buffer (PBS pH 7.4) at 37° C. in a shaker rotated at 100 rev/min. Initially, buffer solution is collected every day for drug analysis, and replaced with new buffer solution. After seven days, the sample is collected every alternate day, with the frequency decreasing to every five days at longer times. The collected samples are kept under the hood overnight to drive off the buffer solution.

The quantification of dendrimer-FA (D-FA) is performed using a C5 silica based HPLC column (250 mm×4.6 mm, 300 Å). (Mohammad T. Islam, X. S. et al., *Anal. Chem.* 77:2063-2070 (2005)) The mobile phase for the elution of D-FA is a linear gradient beginning with 90:10 water/acetonitrile (ACN) at a flow rate of 1 mL/min, reaching 50:50 after 30 minutes. Trifluoroacetic acid (TFA) at 0.14 wt % concentration in water as well as in ACN is used as a counter-ion to make the dendrimer-conjugate surfaces hydrophobic. (Mohammad T. Islam, X. S. et al., *Anal. Chem.* 77:2063-2070 (2005))

The conjugates are dissolved in the mobile phase (90:10 water/ACN). The detection of D-FA in eluted samples is performed at 210 and 238 nm, the $\lambda_{max}$ of PAMAM-G4-OH and FA respectively. The calibration curve is prepared based on 238 nm for FA in the conjugated form. The elution time for D-FA in this system is expected to be at eight minutes. To quantify the possible presence of free FA, a C-18 reverse phase symmetry shield column from Waters is used (3.9× 150 mm column, 5 µm; W20881A). (Glenn J. Jaffe 2000; Glenn J. Jaffe 2000) A 1:1 mixture of acetonitrile and 0.02% sodium acetate (pH 4.0) is used as the mobile phase. The sample is injected at 1 ml/min and the drug FA elutes at around 3.0 minutes. The detection of eluted samples is performed at 238 nm ($\lambda_{max}$ of FA), with an appropriately prepared calibration curve.

Example 11

Pharmacodynamic Efficacy of Hybrid [PLGA-(D-FA) Nanodevice] Microspheres in Maintaining ERG Amplitudes and Photoreceptors in the RCS Rat After collecting and analyzing six months of data from experiments as described in Example 10, this Example is performed to examine the pharmacodynamic efficacy of single PLGA-(D-FA) injections in maintaining ERG b-wave amplitudes and preserving photoreceptor cell counts in aging RCS rats. For this study, PLGA-(D-FA) microspheres are constructed that release D-FA at the release rate that is experimentally validated to be efficacious according to Example 10.

Using the same protocols outlined above for intravitreal injections, one group of five-week RCS rats undergo intravitreal injection of PLGA-(D-FA) microspheres and another group will receive intravitreal injection of PBS containing D-FA and free-PLGA microparticles. Two experimental groups are established of fifteen animals per group. ERG recordings are performed once per month. PLGA-(D-FA) and D-FA+free-PLGA microsphere re-injection are performed when ERG b-wave amplitudes have declined by 10% as compared to the mean of the two-previous ERG recordings. Five animals per group are euthanized at months three, six, and nine for quantitative histological analysis of photoreceptor cell counts, total microglia and microglial localization, as well as number of activated microglia.

PLGA micro spheres (75% PLA/25% PGA) are designed that are intended to release D-FA over a four to six month time, so that the efficacy can be maintained for at least a six month period. A slow-release phase is expected for a sixty to seventy day period, and a somewhat faster release at later times when the particle erodes appreciably. A significantly slower sustained release profile is expected for the nanodevice. Very little initial burst for the D-FA (17 kDa) is expected. For biodistribution, compared to D-FITC, PLGA-D-FITC are expected to show significantly higher intravitreal fluorescence, and significantly lower outer retinal fluorescence at comparable times. D-FITC is expected to be present in the outer retina at much longer times. If in vitro studies show that D-FA is released at a faster rate than desired, then the composition of the PLGA can be changed to 90% PLA/10% PGA, or pure PLA.

Example 12

Electroretinographic Findings Associated with Intravitreal Injections of Dendrimer-Conjugated and Unconjugated Fluocinolone Acetonide in RCS Rats In this Example, the efficacy of D-FA nanodevices was compared to the free drug and comparable drug doses. The efficacy was analyzed using electroretinography (ERG) and histology. The results indicate that just one intravitreal injection of the dendrimer nanodevice at the lowest administered dose, not only prevents ERG reduction, it enhances the ERG levels substantially.

Thirty albino RCS rats aged five weeks were divided into six equal groups. The experiments were terminated at nine weeks. Thus, the efficacy was evaluated over the four-week peak period of retinal degeneration in the RCS rats. The groups were:
1. intravitreal injection of 3.0 µg dendrimer-conjugated fluocinolone acetonide (FA) in 1.0 µL of Phosphate Buffered Solution (PBS);
2. intravitreal injection of 1.0 µg dendrimer-conjugated FA in 1.0 µL of PBS;
3. intravitreal injection of 3.0 µg FA in 1.0 µL of PBS;
4. intravitreal injection of 1.0 µg FA in 1.0 µL of PBS;
5. intravitreal injection of 1 µL of PBS (vehicle control);
6. light-exposed unoperated controls.

Comparison of initial (at five weeks of age) ERG a-wave amplitudes showed no statistically significant difference between experimental groups (p≥1.0). Comparison of endpoint (at nine weeks of age) ERG a-wave amplitudes showed statistically significant differences between right and left eyes of D-FA treated animals. Thus, D-FA preserved photoreceptor response amplitudes in a dose-dependant manner. This was not true for PBS-injected or free-FA injected eyes.

The dendrimer-conjugation enhanced FA's neuroprotective effects over the non-conjugated drug. This phenomenon was also observed for ERG b-wave amplitudes. All FA-treated animals demonstrated the greatest stabilization of ERG b-to-a-wave amplitudes. ERG implicit times were significantly lower in D-FA treated animals as compared to FA-treated, control or untreated animals. This is consistent with the finding that dendrimer conjugation of FA improves its pharmacological efficacy.

The Table below shows ERG a-wave and b-wave amplitude change (Mean±Standard Error) among six experimental groups at the end of the study, as compared to the ERG amplitudes at the beginning of the study (expressed as a percentage of loss (−)/gain (+) from the initial amplitude).

| Experimental Group | ERG a-wave | | ERG b-wave | |
|---|---|---|---|---|
| | OD | OS | OD | OS |
| Dendrimer-FA 3.0 µg | +17.8 ± 18.1% | +30.9 ± 20.1% | −13.8 ± 9.8% | −34.7 ± 13.2% |
| Dendrimer-FA 1.0 µg | +88.6 ± 34.3% | +1.7 ± 11.7% | −15.8 ± 9.9% | −34.3 ± 9.2% |
| Free FA 3.0 µg | −12.5 ± 28.8% | −10.5 ± 30.1% | −42.6 ± 3.3% | −40.8 ± 3.5% |
| Free FA 1.0 µg | −41.9 ± 13.4% | −47.8 ± 7.7% | −64.2 ± 8.6% | −55.6 ± 3.6% |
| PBS | −73.9 ± 2.3% | −76.1 ± 2.4% | −62.9 ± 2.2% | −63.4 ± 2.9% |
| Unoperated | −73.9 ± 4.5% | −79.1 ± 3.9% | −60.8 ± 7.8% | −72.7 ± 4.8% |

The data disclosed in this Example provide additional evidence of the benefits of dendrimer conjugation, as shown in the Table above. For the first time, a-wave amplitudes increase over the period of time where a greater than 75% reduction in amplitudes was observed.

Example 13

Dendrimer Biodistribution and Efficacy and Nanoparticle Biodistribution and Efficacy According to this Example, PAMAM-G4-OH dendrimers showed enhanced uptake in the outer nuclear layer of degenerating RCS rats, but not in normal SD rats, suggesting that they can be used to target neuroinflammation. Retinal biodistribution of free-FITC and dendrimer-conjugated FITC (D-FITC) were studied in healthy Sprague-Dawley (SD) and Royal College of Surgeons retinal degeneration model (RCS) rats with active neuroinflammation.

The first set of results is shown in FIGS. 10A-10F, epi-fluorescence histology from retinal cryosections performed twenty four hours and ten days after intravitreal injection, showing (FIG. 10A) D-FITC distribution in normal SD rats at twenty four hours, and (FIG. 10B) D-FITC distribution in the RCS retinal neurodegeneration model at twenty four hours. The concentration of D-FITC within the outer nuclear layer (denoted by *) and debris zone are significant findings.

Figures 10A, 10B, 10C, 10D, 10E, 10F:
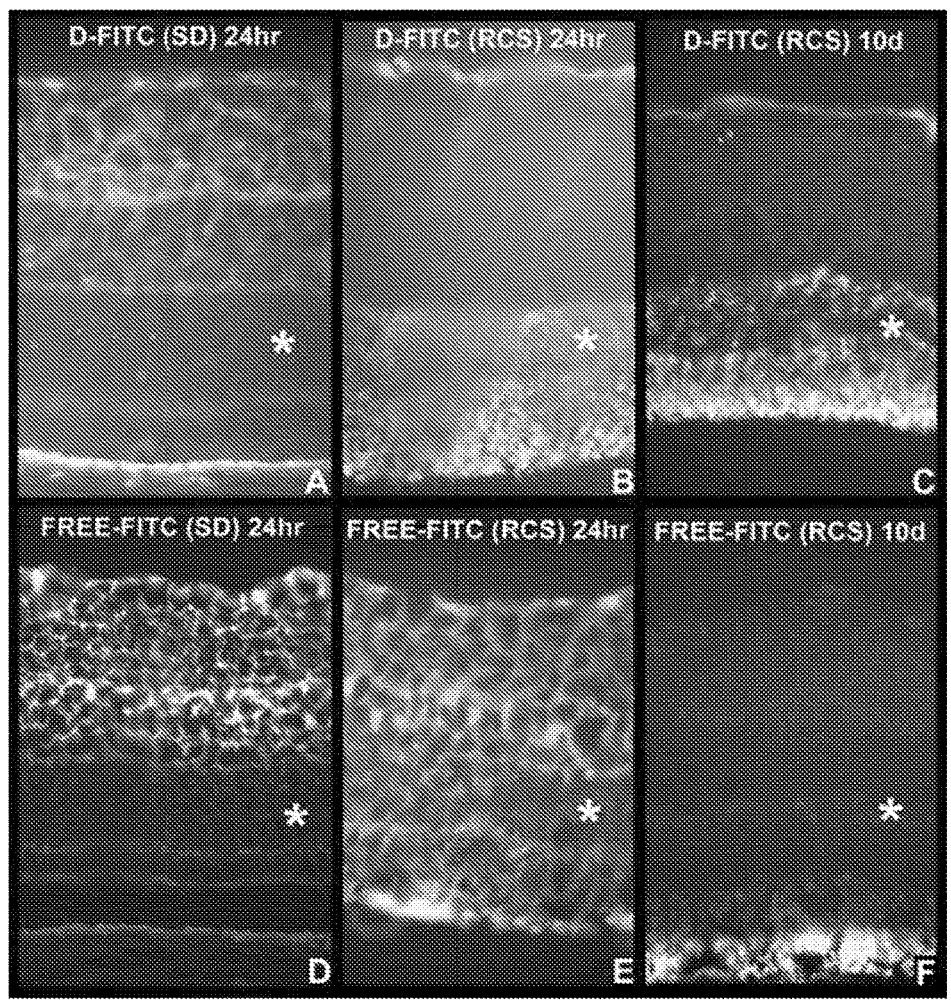
FIGS. 10A-10F show retinal biodistribution of free-FITC and dendrimer-conjugated FITC (D-FITC) in healthy Sprague-Dawley (SD) and Royal College of Surgeons retinal degeneration model (RCS) rats with active neuroinflammation.

In examining the RCS rat retina in FIG. 10B, it is apparent that the D-FITC demonstrated enhanced uptake into the outer retina, precisely located in and among the ONL, activated microglia and outer debris zone. This pattern of uptake was not observed in any of the healthy SD retinas (FIG. 10A and FIG. 10D). Red in the images is due to autofluorescence from the TRITC filter. The retinal pigment epithelium (RPE) demonstrates enhanced FITC fluorescence in retinas that received D-FITC-containing injections. No FITC fluorescence was observed in the RPE of eyes that received free FITC injections. This pattern was qualitatively similar at ten days post injection. The FITC signal present in FIG. 10F is autofluorescence from the outer-debris zone. The RPE has separated from the retina in this image and is not visible.

These data suggest that cells that have high endocytotic rates such as activated microglia and retinal pigment epithelium demonstrate enhanced uptake of D-FITC conjugates. Consequently, the results show that dendrimer-drug conjugates likely demonstrated enhanced uptake in retinal sublaminae undergoing active neuroinflammatory and other neurodegenerative processes. Furthermore, FIG. 10C demonstrates that the dendrimer conjugates are not cleared from the retina as rapidly as free-FITC, FIG. 10F. Thus dendrimer-drug conjugates are capable of prolonging the residence time of drugs in areas of active neuroinflammation, enhancing the pharmacodynamic efficacy, targeting specific retinal sublaminae, reducing the overall amount that must be delivered and potentially reducing side-effects.

The D-FITC localization in the outer-retina was further analyzed by immunohistochemical labeling for activated microglial cells, astrocytes, and Mueller cells and the photoreceptors (as shown in FIGS. 11A-11D, FIGS. 12A-12B, FIGS. 13A-13D, FIG. 14, and FIGS. 15A-15B). The results suggest that dendrimers are selectively localizing in these cells associated with neuroinflammatory processes. There was minimal accumulation in the other cells in the inner and outer retina. FIGS. 11A-11D show Microglial uptake of D-FITC. (FIG. 11A) ED-1 immuno-histochemical labeling of inner-retinal microglial cells; (FIG. 11B) D-FITC uptake within inner retinal microglia (60×); (FIG. 11C) outer retinal ED-1 labeled activated microglia; and (FIG. 11D) D-FITC uptake within activated microglia.

FIGS. 12A-12B provide further results. (FIG. 12A) Glial-acidic fibrillary protein (GFAP) immunostaining of activated retinal astrocytes; and (FIG. 12B) Dendrimer-FITC uptake by activated retinal astrocytes.

FIGS. 13A-13D show that D-FITC is taken up by the activated retinal Mueller glial cells. FIG. 13A shows GFAP labeling of activated retinal Mueller cells in five week RCS rats (lateral view); (FIG. 13B) shows D-FITC uptake by activated retinal Mueller cells (same field as in A), and D-FITC uptake within the retinal capillary (arrow); (FIG. 13C) shows GFAP labeling of retinal Mueller cells (axial view) at inner nuclear layer. The INL cell bodies are particularly notable (outlined by Mueller cells processes); and (FIG. 13D) shows D-FITC uptake by retinal Mueller cells (axial view).

GFAP staining in these cells was specific to the activated phenotype (FIG. 12A). Imaging of the FITC epifluorescence (FIG. 12B) in the same micrographic field shows significant D-FITC uptake. In addition, a small intra retinal capillary is also shown to uptake D-FITC (FIG. 13B, marked by arrow). Co-localization of GFAP and D-FITC was also seen in Mueller cells as their processes pass the outer nuclear layer (FIGS. 13C-13D). FIG. 14 is a photograph that shows uptake of D-FITC by retinal photoreceptors in 5-week RCS rats. Photoreceptors are labeled by D-FITC uptake.

The retinal vasculature demonstrated a high degree of D-FITC uptake (FIGS. 15A-15B), within the vessel walls. This was true for the inner retinal circulation as well as much deeper fine capillaries within the retinal parenchyma.

Nanoparticle biodistribution was also investigated. To study the role of the particles size and the hardness, monodispersed FITC-labeled PS nanoparticles, of size 50 nm and 200 nm were used. The results are shown in FIGS. 16A-16B, which show inner retinal nanoparticle biodistribution in S334-ter-4 rats, seventy two hours after intravitreal injection. Green: FITC-labeled PS nanoparticles, Red: Rhodamine GFAP. (FIG. 16A) 50 nm FITC nanoparticles are seen within astrocyte somata. (FIG. 16B) 200 nm FITC nanoparticles remained confined to the pre-retinal vitreous, and did not appear to be taken into the cells that take up the dendrimer.

The results discussed in the examples above show that: (1) Upon intravitreal injection, the dendrimers selectively localize in the cells primarily associated with neuroinflammation, such as activated microglial cells, Mueller cells, astrocytes and macrophages; (2) the dendrimers appear to be present in these cells, even after weeks; (3) dendrimer-drug conjugate releases the conjugated drugs over a period of a month; (4) the in vivo efficacy of one injection of the dendrimer nanodevice in the vitreous chamber is significantly better than both the free drug and a controlled release implant, over a one-month period. In fact, electroretinography (ERG) measurements suggest that the dendrimer nanodevice, not only prevents further degeneration, it may actually enhancing retinal health.

While the description above refers to particular embodiments of the present invention, it will be understood that many modifications may be made without departing from the spirit thereof. The presently disclosed embodiments are therefore to be considered in all respects as illustrative and not restrictive. All patents and publications referenced are incorporated herein by reference.

What is claimed is:

1. A method of treating ocular neuroinflammation in a subject in need thereof comprising intravitreally administering a dendrimer-drug conjugate to the subject in need thereof,
    wherein the dendrimer-drug conjugate consists of a generation 4 (G4) polyamidoamine (PAMAM) dendrimer-branched polymer having at least one —OH terminal group conjugated to at least one anti-inflammatory agent,
    wherein the dendrimer-drug conjugate is selectively taken up by activated microglial cells at a site of ocular neuroinflammation,
    wherein the dendrimer-drug conjugate provides sustained release of the at least one anti-inflammatory agent for at least one month at the site of ocular neuroinflammation, and
    wherein the effective dosage of the dendrimer-drug conjugate for treatment of ocular neuroinflammation is less than the effective dosage of the free drug administered intravitreally.

2. The method of claim 1 wherein the ocular neuroinflammation is caused by one or more of age-related macular degeneration (ARMD), retinitis pigmentosa, infection, retinal detachment, retinal ischemia, and macular edema.

3. The method of claim 1 wherein the dendrimer-drug conjugate is administered in an amount effective for sustained release of the anti-inflammatory agent over a period of several months.

4. The method of claim 1 wherein the method is neuroprotective of ocular cells as measured by electroretinogram b-wave amplitudes and/or outer nuclear layer cell counts.

5. The method of claim 1, wherein the anti-inflammatory agent is fluocinolone acetonide.

6. The method of claim 1 wherein the dendrimer-drug conjugate is administered in an amount effective for slowing progressive vision loss in a subject due to inflammation.

7. The method of claim 1 wherein the dendrimer-drug conjugate is administered in an amount effective for intracellular release of the anti-inflammatory agent following selective intracellular delivery into the activated microglia.

* * * * *

UNITED STATES PATENT AND TRADEMARK OFFICE
CERTIFICATE OF CORRECTION

PATENT NO. : 10,463,609 B2  
APPLICATION NO. : 12/681516  
DATED : November 5, 2019  
INVENTOR(S) : Kannan Rangaramanujam et al.

Page 1 of 2

It is certified that error appears in the above-identified patent and that said Letters Patent is hereby corrected as shown below:

On the Title Page

Item (75) Inventors, please replace "Bharath Rajaguru" with "Bharath Raja Guru".

In the Specification

Column 2, Line 22, please replace the term "grow" with "grow.".
Column 3, Line 2, please replace the term "17-hyroxypregnenolone" with "17-hydroxypregnenolone".
Column 3, Line 57, please replace the phrase "topical preparation an implanted device" with "topical preparation, an implanted device".
Column 4, Line 15, please replace the phrase "may the vitreous of the eye" with "may be the vitreous of the eye".
Column 4, Lines 15-16, please replace the phrase "may over a period of seconds" with "may be over a period of seconds".
Column 5, Line 57, please replace the term "concentrations" with "concentrations.".
Column 6, Line 10, please replace the term "(FIG. 9B) Mean" with "(FIG. 9B) mean".
Column 12, Line 14, please replace the phrase "on other embodiments" with "in other embodiments".
Column 15, Line 31, please replace the term "(e.g., RNA,molecule)" with "(e.g., RNA molecule)".
Column 15, Line 49, please replace the term "radioisotope.}}" with "radioisotope.".
Column 18, Line 16, please replace the term "A liphatic" with "Aliphatic".
Column 23, Line 42, please replace the term "PANAN-G4-OH" with "PAMAM-G4-OH".
Column 25, Line 12, please replace the term "dell" with "cell".
Column 25, Line 20, please replace the term "retine" with "retina".
Column 27, Line 15, please replace the phrase "drugs like such as" with "drugs such as".
Column 27, Line 20, please replace the term "Da,;" with "Da,".
Column 29, Line 11, please replace the term "6-µm" with "6 µm".
Column 30, Line 1, please replace the term "14 µ" with "14 µm".
Column 30, Line 51, please replace the term "require" with "required".
Column 31, Line 17, please replace the term "that the D-FA" with "as the D-FA".

Signed and Sealed this  
Second Day of February, 2021

Drew Hirshfeld  
*Performing the Functions and Duties of the*  
*Under Secretary of Commerce for Intellectual Property and*  
*Director of the United States Patent and Trademark Office*

Column 38, Line 10, please replace the term "(FIG. 13B)" with "FIG. 13B".
Column 38, Lines 12-13, please replace the term "(FIG. 13C)" with "FIG. 13C".
Column 38, Line 16, please replace the term "(FIG. 13D)" with "FIG. 13D".

In the Claims

Claim 7, Column 40, Line 20, please replace the term "microglia" with "microglial cells".